(12) United States Patent
Kropp et al.

(10) Patent No.: US 8,974,810 B2
(45) Date of Patent: *Mar. 10, 2015

(54) TISSUE GRAFT COMPOSITIONS AND METHODS FOR PRODUCING SAME

(75) Inventors: Bradley P. Kropp, Edmond, OK (US); Hsueh-Kung Lin, Edmond, OK (US); Fadee Mandelek, Oklahoma City, OK (US); Brian P. Grady, Norman, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 512 days.

This patent is subject to a terminal disclaimer.

(21) Appl. No.: 13/195,400

(22) Filed: Aug. 1, 2011

(65) Prior Publication Data
US 2011/0288656 A1     Nov. 24, 2011

Related U.S. Application Data

(60) Continuation of application No. 11/641,388, filed on Dec. 19, 2006, now abandoned, and a continuation-in-part of application No. 11/326,533, filed on Jan. 5, 2006, now Pat. No. 7,507,422, which is a division of application No. 10/314,799, filed on Dec. 6, 2002, now Pat. No. 7,078,033.

(60) Provisional application No. 60/338,608, filed on Dec. 7, 2001, provisional application No. 60/751,745, filed on Dec. 19, 2005.

(51) Int. Cl.
| | |
|---|---|
| *A61L 27/56* | (2006.01) |
| *A61F 2/04* | (2013.01) |
| *A61K 35/38* | (2006.01) |
| *A61F 2/02* | (2006.01) |
| *A61L 27/36* | (2006.01) |
| *A61L 27/38* | (2006.01) |
| *C12N 5/071* | (2010.01) |
| *A61K 35/12* | (2006.01) |

(52) U.S. Cl.
CPC ... *A61F 2/04* (2013.01); *A61F 2/02* (2013.01); *A61K 35/38* (2013.01); *A61L 27/3629* (2013.01); *A61L 27/3679* (2013.01); *A61L 27/3813* (2013.01); *A61L 27/3826* (2013.01); *A61L 27/383* (2013.01); *A61L 27/3882* (2013.01); *A61L 27/3886* (2013.01); *C12N 5/0685* (2013.01); *A61K 35/12* (2013.01); *A61L 2430/22* (2013.01); *C12N 2502/1347* (2013.01); *C12N 2531/00* (2013.01); *C12N 2533/40* (2013.01); *C12N 2533/92* (2013.01); *A61L 2400/12* (2013.01)
USPC .......................... 424/423; 424/489; 424/93.7

(58) Field of Classification Search
None
See application file for complete search history.

(56) References Cited

U.S. PATENT DOCUMENTS

| | | | |
|---|---|---|---|
| 5,645,860 A | 7/1997 | Knapp et al. | |
| 5,695,998 A | 12/1997 | Badylak et al. | |
| 5,762,966 A | 6/1998 | Knapp, Jr. et al. | |
| 5,866,414 A | 2/1999 | Badylak et al. | |
| 6,576,265 B1 | 6/2003 | Spievack | |
| 7,122,200 B2 | 10/2006 | Kropp et al. | |
| 7,531,503 B2 | 5/2009 | Atala et al. | |
| 2002/0087214 A1 | 7/2002 | Kropp et al. | |
| 2002/0155096 A1 | 10/2002 | Chancellor et al. | |
| 2003/0165474 A1 | 9/2003 | Kropp et al. | |
| 2003/0216811 A1 | 11/2003 | Badylak | |
| 2007/0026069 A1 | 2/2007 | Shastri et al. | |
| 2007/0027460 A1 | 2/2007 | Case et al. | |

OTHER PUBLICATIONS

Ferrand et al.; "Directional porosity of porcine smaill-intestinal submucosa"; Journal of Biomedical Materials Research 27:1235-1241 (1993).
Yoo et al.; "Bladder augmentation using allogenic bladder submocosa seeded with cells"; Adult Urol. 51(2):221-225 (1998).
Raofi et al.; "Comparison of Jejunal and Ileal Surveillance Biopsies in a Porcine Model of Intestinal Transplantation"; Transplantation 68(2):188-191 (1999).
Zhang et al.; "'Co-Culture' of Bladder Smooth Muscle and Urothelial Cells on Small Intestinal Submococa (sis): Evaluation of the Best Culture Method for In Vitro Tissue Engineering Techniques"; Pediatrics Journal Supp: Sep. 1999:807-808.
Zhang, Y. et al.; "Coculture of Bladder Urothelila and Smooth Muscle Cells on Small Intestinal Submucosa: Potential Applications for Tissue Engineering Technology"; Journal of Urology 164:928-935 (2000).
Lu et al.; "Muscle-Derived Stem Cells Seeded Into Acellular Scaffolds Develop Calcium-Dependent Contractile Activity That is Modulated by Nicotinic Receptors"; Urology 61:1285-1291, 2003.
Perets et al.; "Enhancing the vascularization of three-dimensional porous alginate scaffolds by incorporating controlled release basic fibroblast growth factor microspheres", Journal of Biomedical Material Research A, vol. 65:489-497 (2003).
Mondalek et al., "The incorporation of poly(lactic-co-glycolic) acid nanoparticles into porcine small intestinal submucosa biomaterials," Biomaterials 29:1159-1166 (2008).
Roth et al., "Bladder regeneration in a canine model using hyaluronic acid-poly(lactic-co-glycolic-acid) nanoparticle modified porcine small intestinal submucosa," BJU Intl 108:148-155 (2010).
Mondalek et al., "Enhanced angiogenesis of modified porcine small intestinal submucosa with hyaluronic acid-poly(lactid-co-glycolide) nanoparticles: From fabrication to preclinical validation," Journal of Biomedical Materials Research A 94A:712-719 (2010).

*Primary Examiner* — Allison Fox
(74) *Attorney, Agent, or Firm* — Dunlap Codding, P.C.

(57) ABSTRACT

A tissue graft composition is described herein that includes a segment of small intestinal submucosa having at least one nanoparticle incorporated therein such that the permeability of the segment of small intestinal submucosa is altered, thereby providing the segment of small intestinal submucosa with a more substantially uniform structure for cell migration and proliferation. The tissue graft composition may further comprise at least one macromolecule incorporated into the nanoparticle. The tissue graft composition may be utilized in seeded or unseeded methods of tissue repair.

20 Claims, 19 Drawing Sheets
(16 of 19 Drawing Sheet(s) Filed in Color)

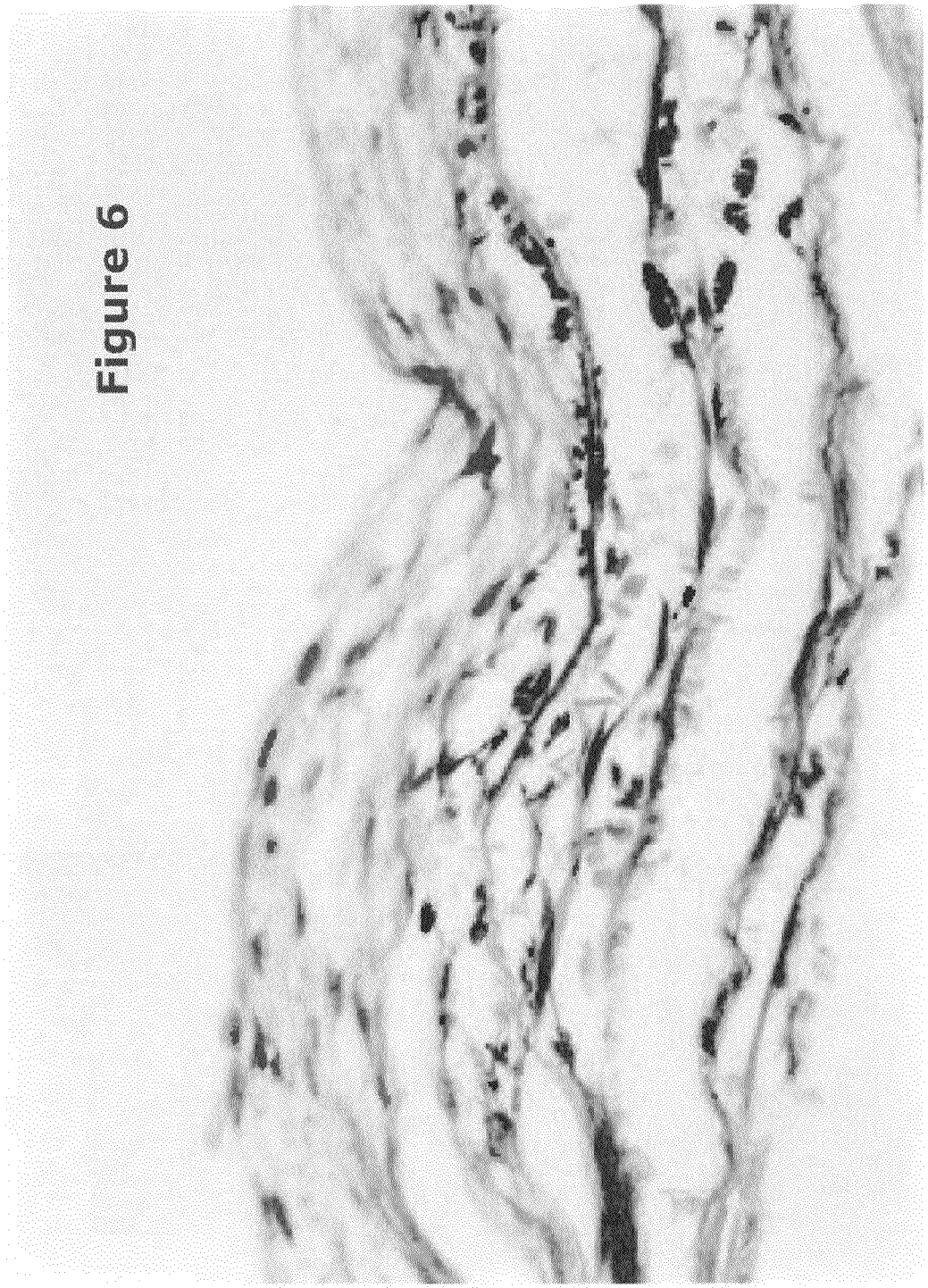

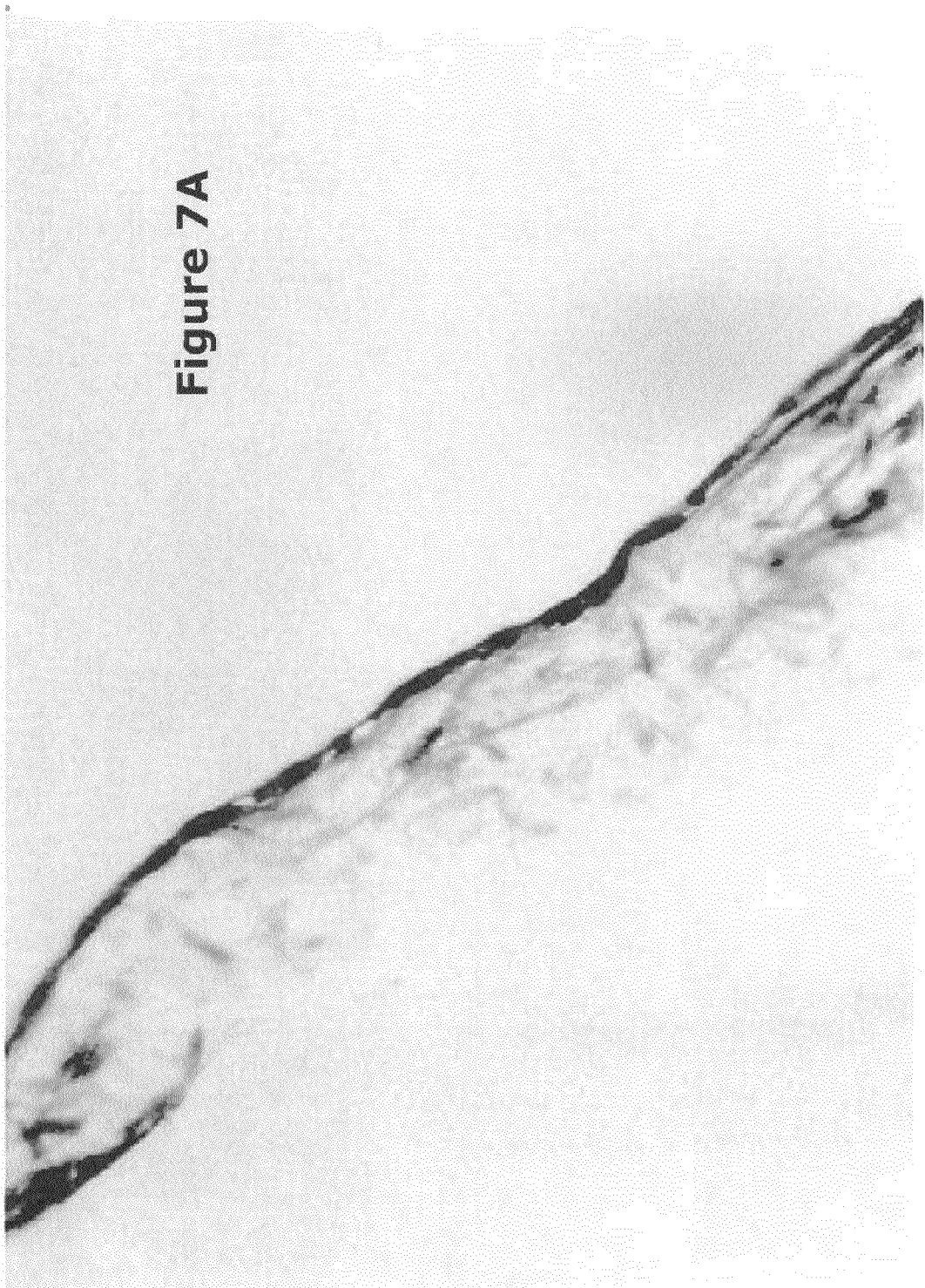

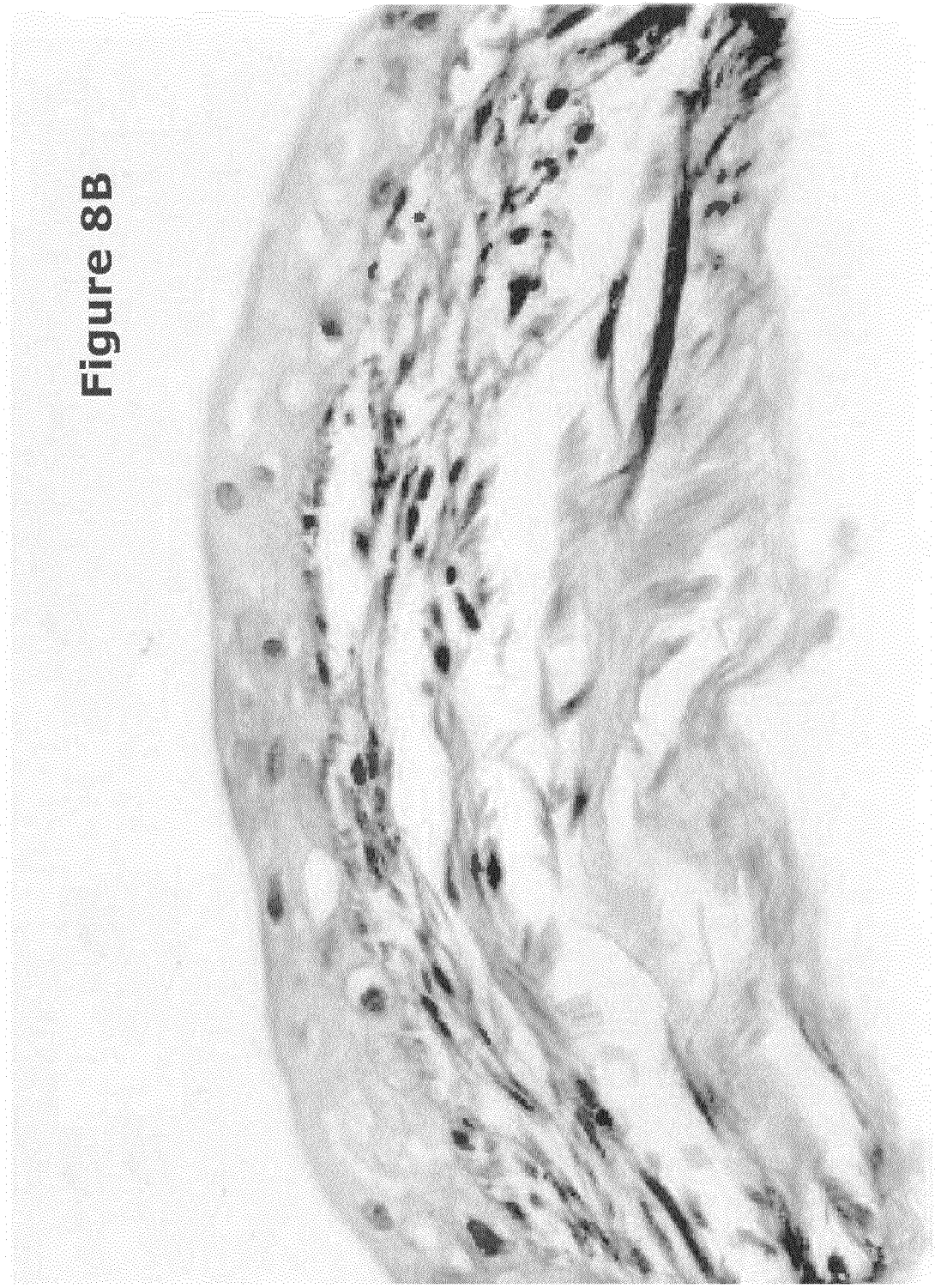

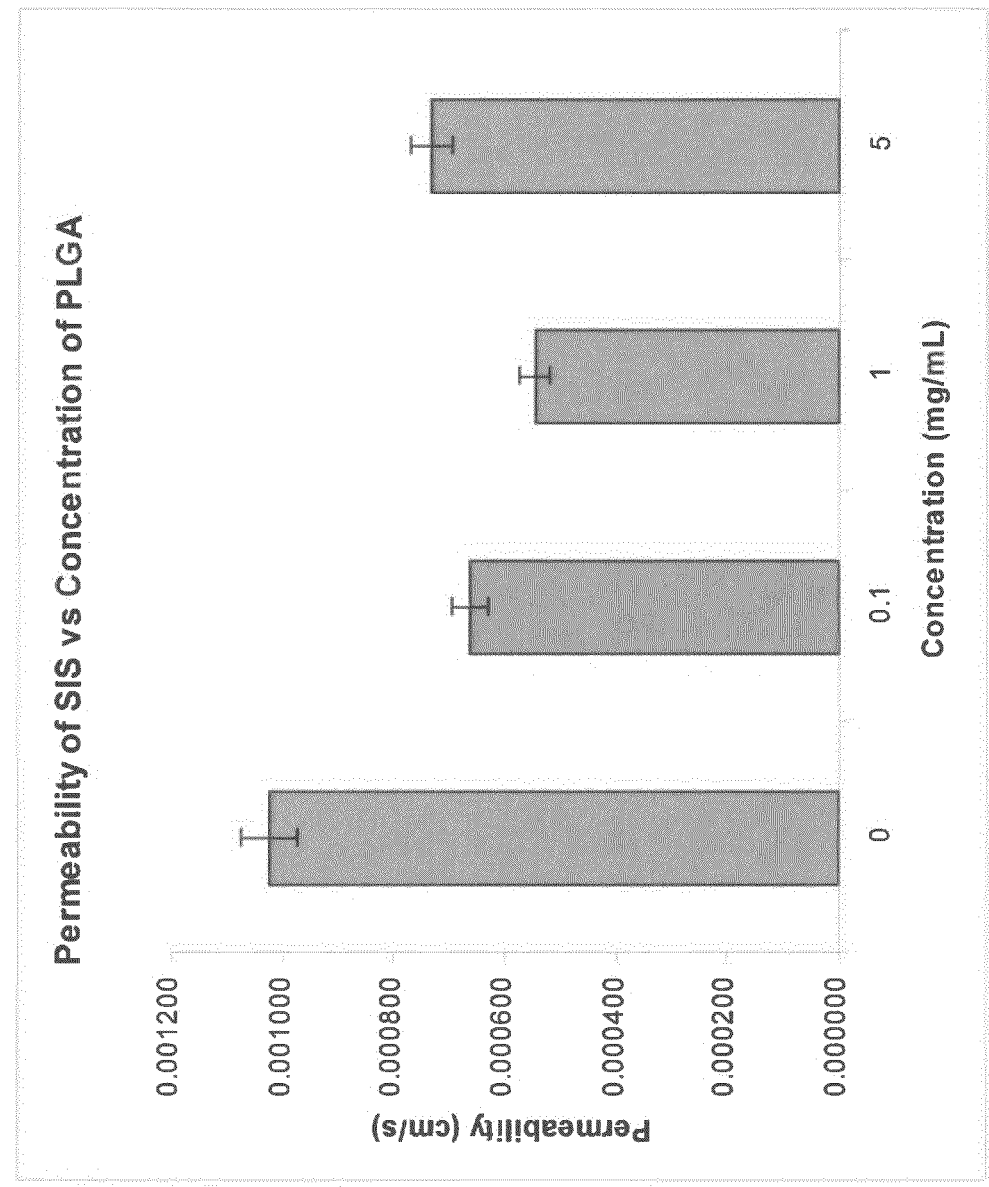

TISSUE GRAFT COMPOSITIONS AND METHODS FOR PRODUCING SAME

CROSS-REFERENCE TO RELATED APPLICATIONS

This application is a continuation of U.S. Ser. No. 11/641,388, filed Dec. 19, 2006, now abandoned; which claims benefit under 35 U.S.C. 119(e) of provisional application U.S. Ser. No. 60/751,745, filed Dec. 19, 2005.

Said application U.S. Ser, No. 11/641,388 is also a continuation-in-part of U.S. Ser. No. 11/326,533, filed Jan. 5, 2006, now U.S. Pat. No. 7,507,422, issued Mar. 24, 2009; which is a divisional of U.S. Ser. No. 10/314,799, filed Dec. 6, 2002, now U.S. Pat. No. 7,078,033, issued Jul. 18, 2006; which claims benefit under 35 U.S.C. 119(e) of U.S. Ser. No. 60/338,608, filed Dec. 7, 2001.

Each of the above-referenced patents and patent applications are hereby expressly incorporated herein by reference in their entirety.

FEDERALLY SPONSORED RESEARCH OR DEVELOPMENT

This invention was made with government support under Contract No. DK 056968 awarded by the National Institutes of Health. The government has certain rights in the invention.

BACKGROUND OF THE INVENTION

1. Field of the Invention

The present invention relates to methods of tissue reconstruction and repair, and more particularly, but not by way of limitation, to improved tissue graft substrates for utilization in seeded and unseeded tissue engineering techniques, as well as methods for producing same.

2. Brief Description of the Related Art

At least twenty-five percent of the clinical problems in pediatric urology are caused by neurologic lesions that affect lower urinary tract function. These clinical presentations are highlighted by urinary incontinence, urinary tract infections and decreased bladder compliance that leads to increased pressure transmission to the upper urinary tract which leads to subsequent renal deterioration. The monetary cost to our health care system of treating children with dysfunctional bladders runs into millions of dollars each year. Therefore, the need for bladder augmentation has increased in both the adult and pediatric population. This increased need requires surgical techniques that are clinically and socially acceptable and allow these children and adults to live a healthier and more normal life. The current methods of treatment of bladder dysfunction leave those goals largely unmet and must be improved if we hope to improve the prognosis of this large population of urology patients.

The gastrointestinal tract has been the autologous tissue source of choice for genitourinary reconstruction in both the adult and pediatric population. Deleterious side effects associated with the use of bowel include infection, intestinal obstruction, mucus production, electrolyte abnormalities, perforation and neoplasia. These potential side effects have ignited tissue engineering research involving bladder reconstruction through bladder regeneration. These endeavors have shown that there is an urgent need for the development of biodegradable materials with predictable behavior and well characterized mechanical properties that can be used as alternatives to gastrointestinal segments for bladder reconstruction. The major obstacle to advancing the field of urinary tract reconstruction and rehabilitation has been the availability of a biomaterial, either permanent or biodegradable, that will function as a suitable scaffold to allow the natural process of regeneration to occur. The ideal graft material would be replaced by the host tissue, promote the development of a structurally intact low pressure reservoir, and serve as a scaffold for the healing and regeneration of the bladder wall. If a suitable exogenous graft material was available, the need for autogenous tissue and all of the negative consequences associated with its harvest could be eliminated. Therefore, investigators continue to search for the proper scaffold and methodology that is necessary to regenerate tissue and maximally restore urinary tract function. Currently, two technologies involving tissue engineering for bladder regeneration and augmentation are being investigated.

The first reconstructive technology, the in vivo or unseeded tissue engineering technique for bladder regeneration, employs xenogenic (derived from stomach, bladder and small intestine) or synthetic biodegradable, acellular matrices. Such tissue engineering technique involves the direct in vivo placement of an unseeded biodegradable material into a host that will then function as a scaffold to allow the natural process of regeneration to occur. While this technology provides the scaffold for wound healing and tissue regeneration, it also requires the host to provide the tissue and proper environment for cell growth and tissue regeneration.

There are two major obstacles for in vivo or unseeded tissue engineering technology for bladder regeneration. The first has been finding a biomaterial that will act as a suitable scaffold for this natural process to occur. Synthetic non-biodegradable biomaterials such as silicone, rubber, polytetrafluoroethylene, and polypropylene have been unsuccessful because of mechanical failure, lithogenesis, or host foreign body reactions (see, e.g., Kudish, *J. Urol.* 78:232 (1957); Ashkar and Heller, *J. Urol.* 98:91 (1967); Kelami et al., *J. Urol.* 104:693 (1970)). As a consequence of failures with non-biodegradable materials, synthetic biodegradable materials have been investigated that would allow the host bladder time for regeneration but then dissolve prior to the onset of any foreign body reaction. These materials have been applied experimentally and have shown improvement over non-biodegradable materials. Xenogenic, collagen-rich biodegradable materials such as placenta, amnion and pericardium have been used with even more encouraging experimental results than studies employing non-biodegradable synthetic materials. However, despite initial encouraging results, none of these materials have been found to be suitable for clinical use. It has been reported that bladders augmented with dura, peritoneum, placenta and fascia contract over time, and that such tissue grafts fail to promote complete bladder wall regeneration (i.e., tissue having a urine impermeable layer and a functional muscle cell layer) (Kelami et al., *J. Urol.* 105:518 (1971)).

The second potential limitation of the unseeded tissue engineering technique for bladder regeneration is that the size of the graft may be limited to the amount of area which can be quickly invested with bladder cells from the remaining native bladder, and therefore may not be sufficient for bladder replacement. If the ratio of the size of the unseeded graft to the amount of native bladder tissue becomes too large, the ability of the animal to invest the graft with smooth muscle cells (SMC) and urothelial cells appears to be compromised. In the absence of quickly covering the graft with bladder cells, contraction and excess scar formation becomes a concern and poor clinical outcomes may result.

Clearly a tissue graft material is desired which is non-immunogenic, not subject to gross shrinkage after implantation, and which promotes the growth of endogenous urinary bladder tissues having a urine impermeable cell layer and a functional muscle cell layer. A collagen-based biomaterial called small intestinal submucosa (SIS) is a xenogenic membrane harvested from small intestine (such as pig small intestine) in which the tunica mucosa is mechanically removed from the inner surface, and the serosa and tunica muscularis are mechanically removed from the outer surface. This produces a thin, translucent graft (0.1 mm wall thickness) composed mainly of the submucosal layer of the intestinal wall. The submucosal layer of animal intestine has an established background in surgery as gut suture. This collagen-rich membrane has been previously shown to function well as an arterial or venous graft eliciting rapid replacement by native tissues. For example, U.S. Pat. No. 4,902,508, issued to Badylak et al. on Feb. 20, 1990, and U.S. Pat. No. 4,956,178, issued to Badylak et al. on Sep. 11, 1990, the contents of which are hereby expressly incorporated herein by reference in their entirety, describe SIS autografts and allografts prepared from the upper jejunum of a dog and used beneficially for vascular constructs.

SIS has also been shown to have excellent host compatibility and remodeling when submucosal bladder injections of minced SIS were performed in pigs (see U.S. Pat. No. 5,275,826, issued Jan. 4, 1994, to Badylak et al., the contents of which are hereby expressly incorporated herein by reference). To date, SIS has been shown to be non-immunogenic with over 1,000 cross-species transplants and direct challenge testing, demonstrating the lack of immunogenicity thereof. Additionally, SIS has been shown to contain a combination of active intrinsic growth factors, cytokines, structural proteins, glycoproteins and proteoglycans that may assist in cell migration and cell to cell interaction as well as cell growth and differentiation during the regenerative process. Based upon these highly desirable characteristics, it appears that SIS has potential as a universal tissue graft.

Initial research using SIS for urinary bladder augmentation was performed in a rat model, and SIS was shown to function as a scaffold to allow the native rat bladder to remodel and regenerate itself. Histologically, the regenerated rat bladders contained all three layers of the bladder (urothelium, smooth muscle and serosa) and were indistinguishable from normal rat bladder at 11 months post-augmentation (Kropp et al., Urology 46:396 (1995)). In addition, in vitro contractility studies showed that strips of in vivo tissue engineered SIS-regenerated rat bladder had contractile properties and nerve regeneration that was similar to the normal rat bladder (Vaught et al., J. Urol. 155:374 (1996)). This was the first evidence that a functional bladder could be achieved with tissue engineering techniques. It also demonstrated that SIS was different than other biomatrix materials that have been studied in the past. Previously, no other material had shown the ability to promote the regenerative capacity of bladder tissue that SIS was demonstrating in the small animal model.

A long term, large animal model evaluating in vivo tissue engineering of SIS bladder augmentation, in which 40% of a canine bladder was removed and replaced with a similar size piece of SIS, demonstrated that the regenerated bladder remained urodynamically compliant with similar capacities as control dogs. There were no deleterious side effects or upper tract changes up to 15 months post-augmentation. Gross examination revealed that all three layers of the bladder had regenerated. However, the quantity and organization of smooth muscle fibers differed slightly from the normal bladder (Kropp et al., J. Urol. 155:2098 (1996)). In vitro contractility bladder strip studies performed on the SIS-regenerated portions of the bladder demonstrated contractile activity and expression of muscarinic, adrenergic and purinergic receptors similar to normal bladder. As was the case in the rat model, SIS-regenerated bladder also demonstrated functional nerve regeneration and innervation that is similar to normal bladder. Finally, in vitro stress/strain compliance studies demonstrated no significant difference between SIS-regenerated bladder and control bladder, both of which were 30-fold more compliant than the original SIS graft material (Kropp et al., J. Urol. 156:599 (1996)).

Critical histological analysis of the regenerated bladder tissue has revealed that the collagen-to-muscle ratio is increased in small intestinal submucosa regenerated bladder compared to normal bladder and that the degree of regeneration is variable within a given graft. The clinical and functional implications of these findings are not clear. In addition, while the obstacle of identifying a biomaterial that will act as a suitable scaffold for the natural process of bladder regeneration to occur is overcome by the use of SIS in unseeded tissue engineering technology, the obstacle of the limited size of a graft formed therefrom still exists.

Further, while small intestinal submucosa has been shown to promote urinary bladder regeneration, in the past, all segments of the small intestine have been used for urinary bladder regeneration, and it was thought that all segments produced similar results. However, commercially available SIS does not provide consistent regenerative properties, and over the last few years multiple problems have been encountered with different small intestinal segments, including calcifications and graft shrinkage, and therefore unreliable and inconsistent results have been obtained in the experimental use of this material for bladder augmentation.

The second tissue reconstruction technology, the in vitro or seeded tissue engineering technique, utilizes biodegradable materials that serve as both a scaffold for the regeneration process to occur as well as cell-delivery vehicles. This technology involves initial harvesting of bladder tissue, such as from a biopsy from host native tissue, to establish primary cultures of bladder cells. Cilento et al. (J. Urol. 152:665 (1994)) demonstrated that it is theoretically possible to expand a transitional epithelial strain to cover the area of an entire football field using this method of cell culture. These cells are then seeded on a biodegradable membrane and, following a period of graft maturation, the in vitro created bladder graft is then transplanted back into the host for continuation of the regeneration process.

In 1992, Atala et al. (J. Urol. 148:658 (1992)) demonstrated the successful use of non-woven polyglycolic acid polymers (PAP) to facilitate the in vitro growth of rabbit and human bladder epithelium and smooth muscle cells. They further demonstrated that human transitional epithelium and smooth muscle cells grown on the biodegradable polymers could then be implanted into athymic mice and grown in vivo, and that the tissue architecture became progressively more complex with time in the animal.

Recently, Yoo et al. (Urology 51:221 (1998)) and Oberpenning et al. (Nat. Biotechnol. 17:149 (1999)) reported on the feasibility of dog bladder augmentation using allogenic bladder submucosa and PAP membranes seeded with urothelial and smooth muscle cells. This study demonstrated that transitional epithelium and smooth muscle cells could be harvested, grown and subsequently seeded on allogenic bladder submucosa for use as augmentation material. Urodynamically, the augmented bladder demonstrated increased capacity during this short term study. Interestingly, the allogenic bladder submucosa which was unseeded also demonstrated the ability to increase bladder capacity; however, the gains in capacity were less than the seeded grafts. Studies such as this as well as those of Atala et al suggest that prior cell seeding of large bladder grafts may be necessary to obtain the best clinical outcome following bladder augmentation. Unfortunately, although the in vitro technique of tissue engineering has been shown to be feasible for both synthetic and xenogenic matrices, thus far no studies have been undertaken to determine the effectiveness of the materials to facilitate the regeneration of functional bladder tissue in a large animal.

In addition, while all segments of small intestinal submucosa have been used to promote urinary bladder regeneration, multiple problems have been encountered with different small intestinal segments, including calcifications and graft shrinkage, and therefore unreliable and inconsistent results have been obtained in the experimental use of this material for bladder augmentation. However, thus far no studies have been undertaken to determine if the effectiveness of one segment of small intestine over another has any effect on the consistency and reliability of the grafts formed therefrom.

Further, no studies have previously been undertaken to determine if SIS can be modified to provide a more uniform structure or modified to incorporate macromolecules that are important for tissue regeneration and thus enhance the tissue regeneration process.

Therefore, there is a need felt within the art to identify new and improved tissue graft substrates that have a substantially uniform structure for cell migration and proliferation and/or that deliver macromolecules for efficient tissue regeneration, as well as methods of making and using same, thereby overcoming the disadvantages and defects of the prior art.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 6 is a photomicrograph illustrating smooth muscle cells grown alone on small intestinal submucosa for 28 days, which exhibit spindle shaped morphology. Cells are 5 to 7 layers thick. Majority of smooth muscle cell growth occurs on the surface of the small intestinal submucosa with areas of minimal matrix penetration just below surface. Reduced from ×94.

FIG. 7 is photomicrographs of urothelial cells grown alone on small intestinal submucosa for 28 days in low calcium conditions (A, 0.09 mM) and physiological levels of calcium (B, 2.5 mM). Urothelial cells in A demonstrate 1 to 2 layers of flattened cells (Trichrome, reduced from ×63). Urothelial cells in B are cuboidal in shape and form multilayered pseudostratified urothelium (reduced from ×78).

FIG. 16 graphically illustrates the permeability of treated SIS to urea, wherein the SIS was treated by incubation with PLGA NPs. Zero on the concentration axis denotes the control where the permeability of the SIS to urea was measured without PLGA NPs.

DETAILED DESCRIPTION OF THE INVENTION

Figure 1:
FIG. 1 contains photographs of a distal SIS-regenerated bladder.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The present invention relates to materials for repairing or augmenting tissues and methods for using same. More particularly, the present invention is related to a tissue graft composition comprising a segment of small intestinal submucosa (SIS) that has been modified to provide a substantially uniform structure for cell migration and proliferation.

An embodiment of the present invention is related to a modified tissue graft composition comprising a segment of small intestinal submucosa (SIS) in which at least one nanoparticle has been incorporated to provide a modified SIS, wherein the modified SIS has an altered permeability, thereby providing the SIS with more substantial structural uniformity for cell migration and proliferation. The at least one nanoparticle may function to deliver at least one macromolecule that will enhance tissue regeneration and/or prevent leakage. Examples of macromolecules that may be utilized in accordance with the present invention include, but are not limited to, genes, mRNAs, proteins, nutrients, drugs, growth factors, hormones, polysaccharides, and combinations or derivatives thereof.

Another embodiment of the present invention is related to a method of producing a tissue graft composition, such as but not limited to a urinary tract tissue graft composition, which closely resembles the architecture of normal tissue. Such tissue graft composition comprises a xenograft of biodegradable porcine small intestinal submucosa (SIS) modified as described herein above. The SIS may further be seeded with at least one cell type. For example but not by way of limitation, the SIS may be seeded with autologously obtained smooth muscle cells and/or urothelial cells to regenerate urinary tissue and restore normal urinary function, as described in detail herein and in the parent applications that have been incorporated herein by reference. Alternatively, the SIS may be seeded with at least one stem cell type, such as embryonic stem cells or adult stem cells, such as but not limited to, bone marrow stromal cells. The seeding of stem cells on SIS for the production of a urinary tract tissue graft composition, and methods of use thereof, are described in detail in parent application U.S. Ser. No. 10/631,168, which was published as US 2004/0091461 A1, on May 13, 2004 (the entire contents of which have previously been incorporated herein by reference).

The use of SIS in the method of the present invention is considered to have enhanced regenerative potential over the prior art use of PAP. SIS has been shown to have a rich supply of growth factors that have been shown in vitro to support the growth and differentiation of bladder cells. PAP lacks these factors. In addition, a much larger number of cells would be required to seed a segment of PAP compared to the same size segment of SIS. Therefore, SIS should provide a better environment and framework for the regenerative process, and therefore overcomes the defects and disadvantages of the prior art.

In addition, the modified SIS is considered to have enhanced regenerative potential over the currently commercially available SIS. The commercially available, machine-made SIS shows inconsistency in tissue regeneration due to the lack of uniform structure and dispersement of growth factors. The present invention uses nanoparticles to fill in "holes" in the SIS and thus alter the permeability thereof to provide a more uniform structure for cell migration and proliferation, thus decreasing and/or preventing leakage through the tissue graft. Therefore, the SIS of the present invention has decreased permeability when compared to commercially available SIS. In addition, the nanoparticles may further have macromolecules incorporated therein, such as but not limited to, growth factors, hormones, nucleic acids, genes, polysaccharides, drugs, or combinations thereof, which will further enhance the tissue regeneration process.

A nonextractable, autoclave sterilizable tissue culture frame developed for use in the SIS-supported autoaugmentation protocol for production of the urinary tract tissue graft composition of the present invention has been described in parent patent application U.S. Pat. No. 7,122,200, issued to Kropp et al. on Oct. 17, 2006, the contents of which are hereby expressly incorporated herein by reference. In particular, FIGS. 1-12 and Column 7, line 50 through Column 8, line 30 of the '200 patent illustrate examples of tissue culture frames that may be utilized in accordance with the present invention. However, it is to be understood that such examples of tissue culture frames are not to be regarded as limiting, and any other tissue culture frame that is commercially available or otherwise known in the art may be utilized in accordance with the present invention. The only requirements for a tissue culture frame utilized in accordance with the present invention are that the tissue culture frame be sterilizable, that the tissue culture frame allow a segment of SIS membrane to be suspended therein, and that the tissue culture frame hold such segment of SIS membrane in a taut position such that cells may be seeded thereon.

In one embodiment, the method of the present invention involves isolation and culture of smooth muscle and urothelial cells, such as bladder smooth muscle cells (BSMCs) and bladder urothelial cells (BUCs), from a biopsy specimen by collagenase digestion of the tissues. That is followed by seeding smooth muscle cells at a density of $1 \times 10^5$ cells/cm$^2$ on a mucosal surface of the distal ileal segment of SIS membrane which is suspended, under tension, between the frame portions of the tissue culture frame for one hour. Following the one hour period, the tissue culture frame and SIS membrane are turned over, and urothelial cells are seeded at an equal density on a serosal surface of the SIS membrane. An alternate protocol is to seed the smooth muscle cells on the mucosal surface of the SIS sheet and following a one hour period for the cells to attach to the membrane, the urothelial cells are seeded upon the attached smooth muscle cells. In both cases, the graft is then allowed to mature for 14 days in culture. At that point, smooth muscle and urothelium are maximally differentiated and are ready to be implanted back into the tissue donor.

While the urinary tract tissue graft composition described in Example 2 below is formed from bladder cells, it is to be understood that the smooth muscle cells and urothelial cells of the urinary tract tissue graft composition of the present invention may be obtained from any urinary tract tissue, including but not limited to, ureter, urethra, and tunica albuginea.

In another embodiment, the present invention further includes a method for repairing a damaged or diseased tissue of a subject. The method may involve providing a tissue graft composition comprising a segment of small intestinal submucosa having at least one nanoparticle incorporated therein, and contacting the damaged tissue with the tissue graft composition under conditions such that growth of the tissue occurs and the damaged tissue is repaired, thereby restoring function to the tissue.

In yet another embodiment, the present invention includes a method for repairing a damaged or diseased urinary tract tissue of a subject. The method may involve the unseeded technique as described herein above; alternatively, the method may involve isolating and culturing smooth muscle and urothelial cells from a urinary tract tissue specimen of a subject to provide primary cell cultures. The smooth muscle cells are first seeded on a mucosal surface of a distal ileal segment of small intestinal submucosa which is positioned in the tissue culture frame such that the distal ileal segment of small intestinal submucosa is suspended and held in a taut position by the tissue culture frame. The urothelial cells are then seeded on a serosal surface of the distal ileal segment of small intestinal submucosa. Alternatively, the urothelial cells may be seeded on top of the smooth muscle cells attached to the mucosal surface of the distal ileal segment of small intestinal submucosa. The graft formed therefrom is then allowed to mature in culture. Then the distal ileal segment of small intestinal submucosa is removed from the tissue culture frame and contacted with the damaged urinary tract tissue under conditions such that growth of the urinary tract tissue occurs and the damaged urinary tract tissue is repaired, thereby restoring urological function.

Contemporary attempts to use tissue engineering techniques to create tissue for grafting have relied on the use of synthetic matrices as a scaffold on which to seed cells. A significant disadvantage to this approach is the vast quantity of cells which must be obtained to seed the membrane due to low seeding efficiency. The low levels of cell seeding efficiency greatly reduce the utility of the approach. The procedure to isolate sufficient quantities of cells is very invasive and carries an increased risk of surgical complication.

The novelty of the methods of the present invention is readily apparent when viewed in light of traditional attempts to generate functional urinary tissue where little or none had previously existed. Traditional treatment requires two significant surgical procedures, resection of the bowel and subsequent use of the autograft to augment the size of the bladder. Each procedure is associated with a significant risk of complications. It has been demonstrated that enough tissue is obtained from a moderately invasive uroscopic biopsy to isolate a sufficient quantity of cells to seed the membrane in preparation for grafting. The tissue culture frame utilized in the method of the present invention allows the cells to continue to proliferate as well as mature into the desired tissue sheets. Therefore, by using certain embodiments of the method of the present invention, the overall trauma of the process of bladder augmentation is reduced by approximately 50%. Further, the risk of stone formation and malignancy in the regenerated bladder is significantly reduced.

In yet another embodiment of the present invention, a tissue graft composition is provided, as well as a method for producing same. The tissue graft composition comprises a distal ileal segment of SIS isolated from a mature adult pig. The term "distal ileal segment of SIS" is defined herein as a segment of small intestinal submucosa selected solely from the distal segment of the ileum and wherein the distal ileal segment has been isolated away from the duodenum, the jejunum and the proximal ileum of the small intestine, and wherein the distal segment was located within about 300 cm of the terminal ileum and closely associated with Peyer's patches, although Peyer's patches were not included in the segment. The tissue graft composition may be modified by incorporation of at least one nanoparticle therein to alter the permeability thereof and thereby provide a more substantially uniform structure for cell migration and proliferation thereof. The tissue graft composition described above may be utilized in a method of repairing a damaged or diseased tissue by promoting growth of endogenous tissues, such as but not limited to, urinary tract tissues having a urine impermeable layer and a functional muscle layer. The method includes surgically removing the damaged or diseased portion of tissue and replacing the removed portion of tissue with the tissue graft composition described above, and wherein replacing the removed portion of tissue with the tissue graft composition results in promotion of growth of endogenous tissues while reducing the possibility of calcifications or stone formations as well as preventing any substantial reduction in graft size.

In a further embodiment of the present invention, a tissue graft composition is provided, as well as methods for making and using same. The tissue graft composition includes any segment of SIS described herein or known in the art (such as but not limited to, a distal ileal segment of SIS), wherein at least one nanoparticle has been incorporated therein, wherein the incorporation of the at least one nanoparticle improves the biomechanical properties of the SIS and provides the SIS with a more uniform structure to prevent leakage and to promote cell migration and proliferation onto the SIS, thereby promoting successful augmentation of the tissue/organ in which the tissue graft composition is implanted.

The use of nanoparticles to fill in "holes" in SIS will alter the permeability of the SIS and provide a more uniform structure for cell migration and proliferation. More importantly, the inclusion of nanoparticles into the matrices within the SIS can prevent leakage through the graft, for example but not by way of limitation, leakage of urine when the tissue graft is utilized as a urinary tract tissue graft. Urine leakage from a graft causes inflammation and results in regeneration failure.

The term "nanoparticle" as used herein refers to a particle having dimensions of from about 1 to about 5000 nanometers, and having any size, shape or morphology. In one embodiment, the nanoparticles may have a size in a range of from about 200 nm to about 500 nm; however, this size range may vary depending on the type of tissue repair or regeneration for which the tissue graft is utilized, as well as the tissue grafting technique utilized (i.e., seeded or unseeded). In one embodiment, the nanoparticles must be biocompatible with the tissue graft as well as its surroundings, such that the nanoparticles will not be recognized by the host's immune system as foreign. The nanoparticles must be provided with appropriate concentrations of components and appropriate surface charges, based upon the tissue/organ in which the tissue graft will be implanted. The nanoparticles utilized in accordance with the present invention may be naturally occurring, commercially available nanoparticles, or the nanoparticles may be synthesized for use in accordance with the present invention, as described herein below and as known in the art. Particular examples of nanoparticles that may be utilized in accordance with the present invention include, but are not limited to, poly(lactic-co-glycolic) acid (PLGA) nanoparticles, poly lactic acid (PLA) nanoparticles, Chitosen nanoparticles, liposomes, and derivatives or combinations thereof.

In one embodiment, the at least one nanoparticle may further comprise at least one macromolecule (or a gene encoding such macromolecule) for the purpose of delivering genes, proteins and/or drugs into the SIS to enhance the tissue regenerative properties of SIS. The incorporation of the macromolecules into the nanoparticles provides controlled release kinetics for the macromolecules based on the properties of the nanoparticles. For example but not by way of limitation, the at least one macromolecule or gene may include a native growth factor, a recombinantly-produced growth factor, a cDNA encoding such growth factor, and the like. Particular examples of macromolecules that may be utilized in accordance with the present invention include, but are not limited to, growth factors such as but not limited to, vascular endothelial growth factor, cytokines, fibroblast growth factor, nerve growth factor, epidermal growth factor, and the like; hormones; nucleic acids and genes, such as those encoding growth factors; polysaccharides such as but not limited to hyaluronic acid; drugs; and derivatives or combinations thereof. Methods of incorporating macromolecules into and/or on the surface of nanoparticles are known in the art, and are described in detail in Yi et al. (*J. Of Clinical Pharmacy and Therapeutics*, 31:43-48 (2006)); Astete and Sabliov (*Particulate Science and Technology*, 24:321-328 (2006)); and Nam et al. (*Biotechnology Letters*, 24:2093-2098 (2002)); the contents of each of which are hereby expressly incorporated herein by reference. Therefore, no further discussion on specific methods of incorporation of macromolecules into nanoparticles is deemed necessary.

The present invention also includes methods of repairing a damaged tissue of a subject by providing the tissue graft composition having at least one nanoparticle incorporated therein, and contacting the damaged tissue with the tissue graft composition such that growth of the damaged tissue occurs and the damaged tissue is repaired, thereby restoring function of the damaged tissue. The method may further include seeding cells, such as but not limited to, smooth muscle, urothelial and/or stem cells (such as embryonic or adult stem cells), on the tissue graft composition prior to contact with the damaged tissue, wherein the methods of seeding cells are performed as described in any of the patent applications incorporated herein by reference and as described herein previously. Alternatively, the methods of the present invention may be performed without prior cell seeding on the tissue graft composition having at least one nanoparticle incorporated therein.

While particular examples of the present invention relate to the use of the tissue graft compositions of the present invention in a method of repairing urinary tract tissue, it is to be understood that the present invention is not limited to use in repairing urinary tract tissue; rather, the tissue graft compositions of the present invention may be utilized to repair any desired human or veterinary tissue or organ, including but not limited to, skin, bladder, kidney, ligaments, and other tissues and organs, as described in U.S. Pat. Nos. 4,902,508 and 4,956,178, which have previously been incorporated herein by reference, and as otherwise known in the art.

Examples are provided hereinbelow. However, the present invention is to be understood to not be limited in its application to the specific experimentation, results and laboratory procedures described herein below. Rather, the Examples are simply provided as one of various embodiments and are meant to be exemplary, not exhaustive.

Example 1

Materials and Methods

Isolation of Distal Ileal Segment of SIS.

The entire small intestine of a pig greater than three years of age (i.e., a sow) was obtained, and the terminal ileum was identified. The bowel was then thoroughly cleansed with water. The cleansed bowel was opened on the antimesenteric borders, and the terminal portion of the bowel was inspected. There were clear areas of Peyer's patches, and the areas just adjacent to Peyer's patches were used. These areas were thoroughly stripped of mucosa using a gauze sponge and mechanical force. The serosa muscle layers were also stripped using a gauze sponge and mechanical abrasion. The remaining submucosa layer of the small intestine was placed in 0.1% paracetic acid and 20% ethanol for twelve to twenty-four hours. The material was then thoroughly rinsed and placed in sterile water. Only bowel that was within 300 cm of the terminal ileum and only bowel that was closely associated with Peyer's patches was utilized. Peyer's patches were not included in the material itself.

Animal Operation

Using the canine subtotal cystectomy model, animals underwent urinary bladder augmentations with unseeded proximal or distal SIS grafts as described herein previously. Briefly, a 40% cystectomy of the dog bladder was performed, leaving the posterior plate of the bladder remaining. A single layer (0.1 mm thickness) of SIS was sutured to full thickness posterior bladder plate with water-tight running chromic suture.

The proximal and distal SIS-regenerated bladders were harvested 10 weeks after augmentation and fixed in 10% neutral buffered formalin over 24 hours. The tissue samples were studied with hematoxylin-eosin and immunohistochemical staining.

Results/Discussion

Small intestinal submucosa has been shown to promote urinary bladder regeneration. In the past, all segments of the small intestine have been used for urinary bladder regeneration, and it was thought that all segments produced similar results. However, over the last few years multiple problems have been encountered with different small intestinal segments, including calcifications and graft shrinkage, and therefore unreliable and inconsistent results have been obtained in the experimental use of this material for bladder augmentation. Therefore, an object of the present invention was to determine if the swine source and/or the segment of intestine were important in creating consistent and reliable urinary bladder regeneration. U.S. Pat. No. 6,206,931, issued to Cook et al. on Mar. 27, 2001, the contents of which are hereby expressly incorporated herein by reference in their entirety, states that a most preferred source of whole small intestine is harvested from "mature adult pigs weighing greater than about 450 pounds". Tables I-II demonstrate that harvesting small intestine from an older pig, that is, a sow, in conjunction with the use of the distal ileal segment of the small intestine, produces much improved bladder regeneration.

The term "distal ileal segment of SIS" is defined herein as a segment of small intestinal submucosa selected solely from the distal segment of the ileum and wherein the distal ileal segment has been isolated away from the duodenum, the jejunum and the proximal ileum of the small intestine, and wherein the distal segment was located within about 300 cm of the terminal ileum and closely associated with Peyer's patches, although Peyer's patches were not included in the segment.

Figure 2:
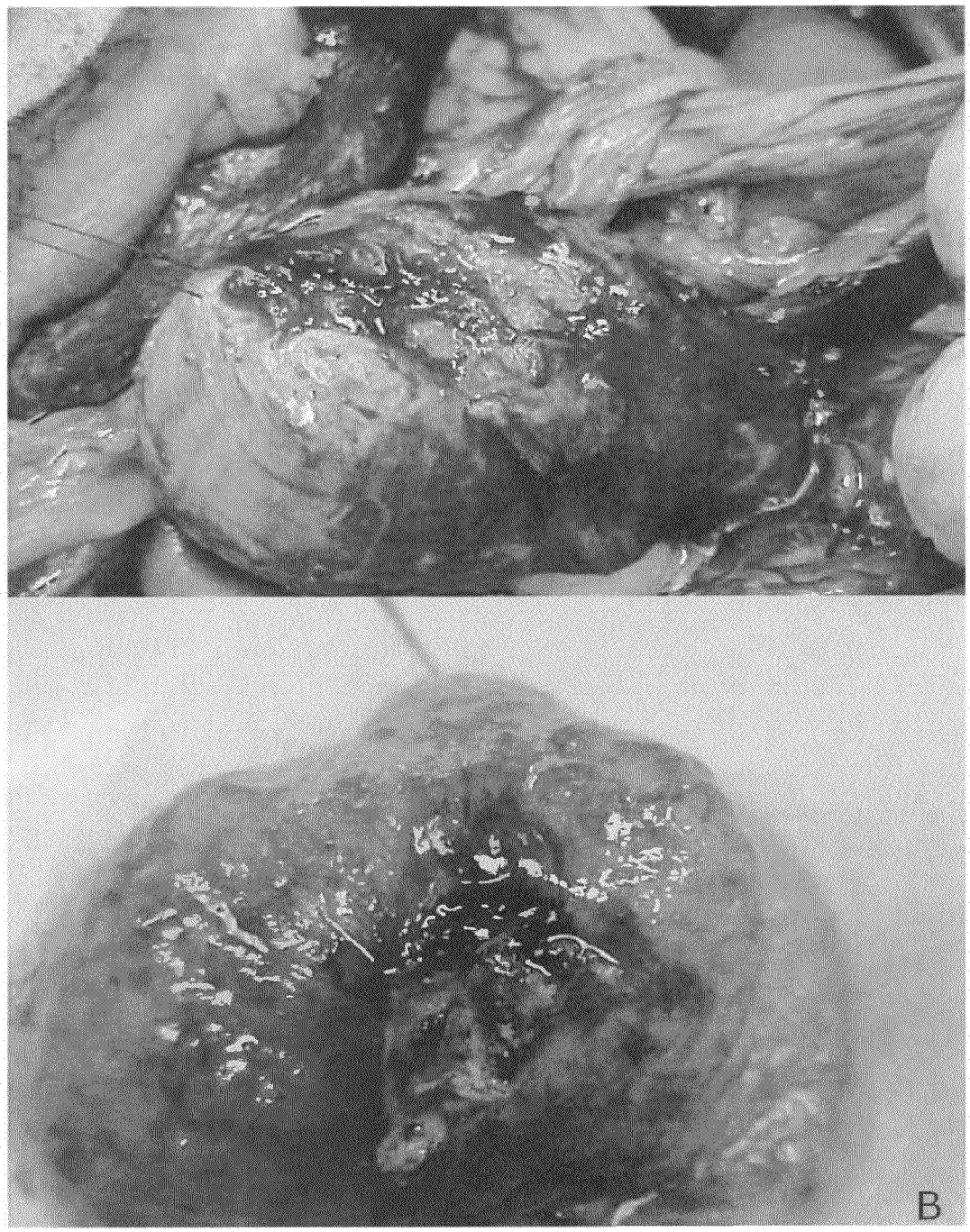
FIG. 2 contains photographs of a proximal SIS-regenerated bladder.

FIGS. 1 and 2 compare the gross morphological appearance of distal SIS-regenerated bladder (FIG. 1) and proximal SIS-regenerated bladder (FIG. 2). The distal SIS-regenerated bladder has a normal spherical shape, while heavy adhesion and shrinkage are evidenced in the proximal SIS-regenerated bladder. In addition, there are less calcifications that develops within the distal SIS-regenerated urinary bladder as compared to the proximal SIS-regenerated bladder. FIG. 2B shows the formation of stones in the proximal SIS-regenerated bladder.

TABLE I

Study on Proximal v. Distal Portion SIS, 10-Week Grafts in Dogs
(Post-Op evaluations 0 = worst; 2 = best)

| | Proximal Portion SIS Graft | | | Distal Portion SIS Graft | | |
| --- | --- | --- | --- | --- | --- | --- |
| Dog # (Pathology #) | #4028 (313) | #3899 (322) | #3813 (340) | ICJ-0 (298) | AHJ-0 (299) | 3853 (301) |
| Grossly: | | | | | | |
| Adhesion | 1 | 1 | 1 | 1.5 | 1 | 1.5 |
| Ureter Displace | 2 | 1 | 1 | 2 | 2 | 1.5 |
| Graft Size | 1 | 1.5 | 1 | 2 | 2 | 2 |
| Softness | 2 | 1 | 1 | 2 | 2 | 2 |
| Calcification within SIS | 2 | 0 | 0 | 2 | 2 | 2 |
| Stone in Bladder | 2 | 0 (many sandy stones) | 2 | 2 | 2 | 2 |
| Microscopically: | | | | | | |
| Urothelium reg | 2 | 2 | 2 | 2 | 2 | 2 |
| SMC bundle | 1.5 | 1.5 | 1.5 | 1.5 | 2 | 2 |
| SMC reg | 1.5 | 1.5 | 1.5 | 1.5 | 2 | 2 |
| Calcification | 2 | 0 | 0 | 2 | 0 (tiny cal) | 2 |
| Neo-vascularization | 2 | 2 | 2 | 2 | 2 | 2 |

TABLE II

Study on Proximal v. Distal Portion SIS from Three Pigs
(Post-Op evaluations 0 = worst; 2 = best)

| | Pig #1 | | Pig #2 | | Pig #3 | |
| --- | --- | --- | --- | --- | --- | --- |
| Dog # (Pathology #) | #4961 (427) | #4692 (424) | #5021 (429) | 4693 (430) | 5024 (426) | 5023 (431) |
| Distal from ileum-cecum (cm) | 400-420 | 260-280 | 100-120 | 200-220 | 100-120 | 200-220 |
| Grossly: | | | | | | |
| Adhesion | 1.5 | 1.5 | 1.5 | 1.5 | 1.5 | 1.8 |
| Ureter Displace | 2 | 2 | 2 | 1.5 | 2 | 2 |
| Graft Size | 1.5 | 1.5 | 1 | 1.5 | 1.5 | 2 |
| Softness | 1.5 | 1.5 | 1.5 | 2 | 1.5 | 2 |
| Calcification within SIS | 0 (tiny cal) | 2 | 0 | 2 | 2 | 2 |
| Stone in Bladder | 0 (sandy stones) | 2 | Undigested SIS | 0 | 2 | 0 |
| Microscopically: | | | | | | |
| Urothelium reg | 2 | 2 | 2 | 2 | 2 | 2 |
| SMC bundle | 1.5 | 1.5 | 1.0 | 2 | 1.5 | 1.5 |
| SMC reg (poor reg) | 1.5 | 1.5 | 1.0 | 2 | 1.5 | 1.5 |
| Calcification | 0 (tiny cal) | 2 | 2 | 2 | 0 (tiny cal) | 2 |
| Neo-vascularization | 2 | 2 | 1.5 | 2 | 2 | 2 |

Figure 3:
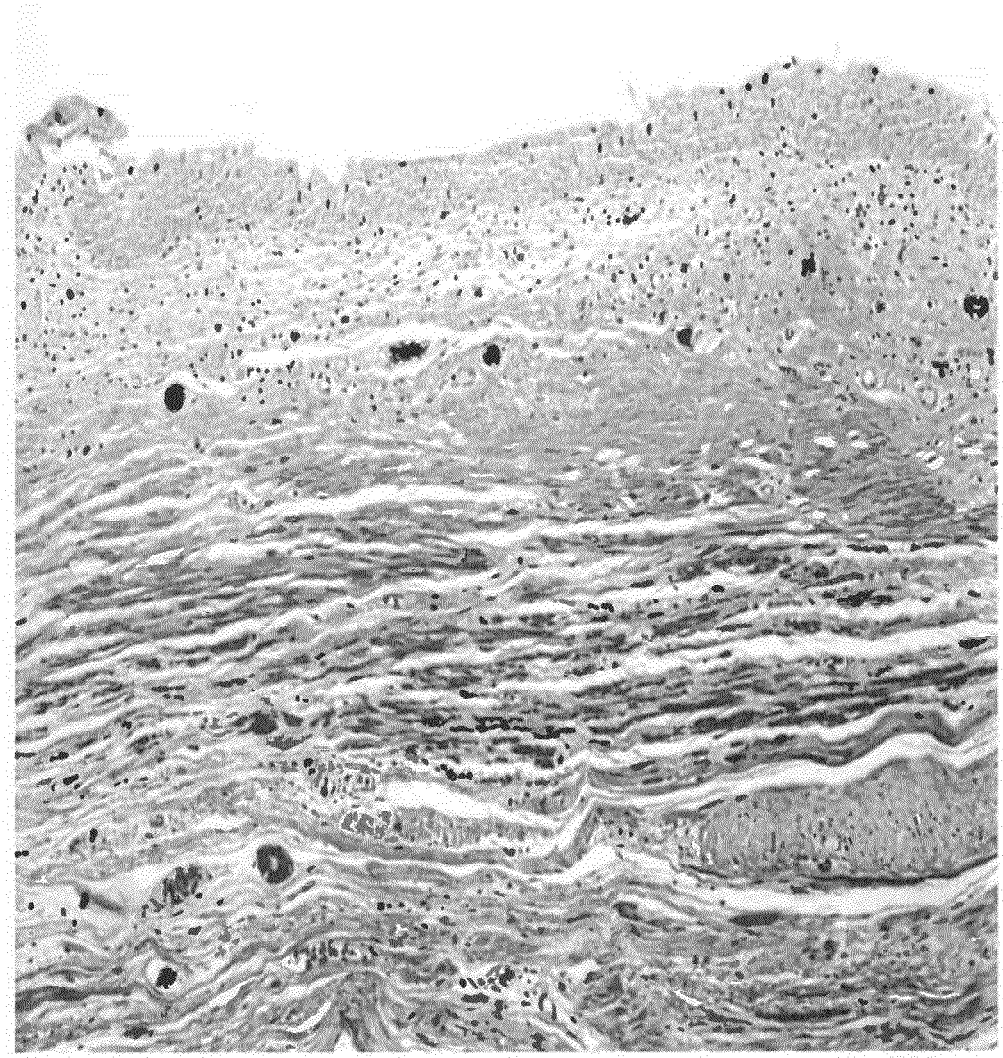
FIG. 3 is a photomicrograph of Masson trichrome stained distal SIS-regenerated dog bladder at 10 weeks postaugmentation. All layers of bladder are present. Abundant smooth muscle bundle formations (red) are surrounded by collagenous matrix (blue). ×10.
Figure 4:
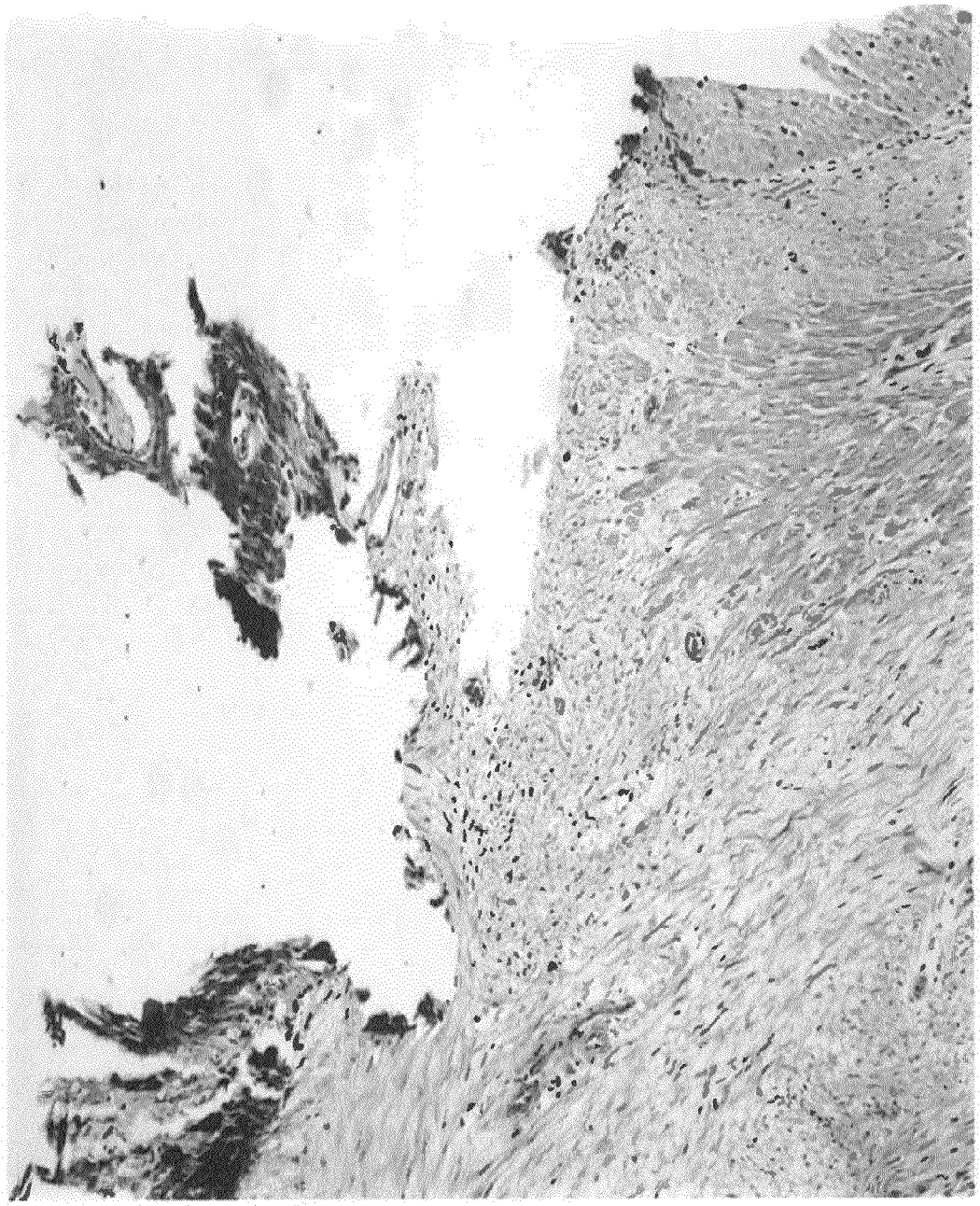
FIG. 4 is a photomicrograph of Masson trichrome stained proximal SIS-regenerated dog bladder at 10 weeks postaugmentation. There is calcification formation on the mucosal layer and limited smooth muscle bundle formation among submucosa and muscle layers. ×10.

FIGS. 3 and 4 are photographs of Masson's trichrome stained SIS regenerated bladder tissue using distal SIS (FIG. 3) and proximal SIS (FIG. 4). In the distal SIS-regenerated bladder (FIG. 3), all layers of bladder are present. Mild diffuse mononuclear cells infiltrate directly and are subjacent to intact normal mucosal urothelial cells. The submucosa contains areas of neovascularization. Smooth muscle bundles (red) are abundant and have a typical layered organization and are surrounded by a collagenous matrix (blue) in the smooth muscle layer. In the proximal SIS-regenerated bladder (FIG. 4), there is calcification formation on the mucosal layer and limited smooth muscle bundle formation among the submucosa and muscle layers.

Thus, several advantages exist for using the distal ileal segment of SIS: there are less calcifications and adhesions that develop within the regenerated urinary bladder, and graft shrinkage is markedly reduced when using this proper segment of SIS from an older animal. Prior to this work, it was thought that all segments of SIS were the same; however, the present invention clearly demonstrates a benefit and an improvement over pre-existing knowledge that the distal ileal segment submucosa of a mature adult pig has enhanced urinary bladder regeneration.

Example 2

Materials and Methods

Tissue Samples.

Human bladder specimens were obtained from 11 patients 2 to 11 years old with primary vesicouretal reflux undergoing open operations for ureteral reimplantation. None of the patients had clinical evidence of bladder dysfunction or neuropathic bladder. A small portion of the tissue was sent for routine histology and the remainder was used to establish primary cultures. Bladder tissue was obtained and processed in conjunction with approval from the Institutional Review Board.

Tissue samples from dog bladders were obtained from five adult male beagles (weighing between 11 and 13 kg) undergoing partial cystectomy for bladder augmentation and were used for establishing primary cell cultures. Bladder tissue was obtained and processed in conjunction with approval from the Institutional Animal Care and Use Committee.

Establishment of Primary SMC and UC Cultures.

Under the dissecting microscope the bladder mucosa was dissected off of the underlying muscle tissues using microscissors. Individual portions of mucosa and muscle tissue were then minced into fine pieces (0.5 mm$^2$) and digested with 200 units/ml collagenase IV. Individual cell suspensions were washed twice with Hank's balanced salt solution, suspended and plated on T25 PRIMARIA® cell culturing flasks. Primary cultures of urothelial cells were established in keratinocyte serum-free media (KSFM) (0.09 mM/L calcium), and SMC were cultured in modified M199 media supplemented with 10% fetal bovine serum (FBS). The cultures were incubated in a humidified 5% $CO_2$ air atmosphere at 37° C. The cells were fed with fresh media every 2 days thereafter. Once cultured urothelial cells achieved 90 to 100% confluence, they were harvested with 0.05% trypsin/EDTA and routinely passaged. Further subculturing and passaging were done in a routine fashion. Human UC and SMC used for seeding on small intestinal submucosa were between passages 2 and 8, while dog UC and SMC used for tissue culture on small intestinal submucosa were all below passage five at the time of seeding.

Small Intestinal Submucosa Disks.

Human bladder cells were seeded and grown on commercially available small intestinal submucosa disks. These 1 cm disks were manufactured in a manner such that the small intestinal submucosa is suspended over a circular polypropylene frame (border 5 mm on top and 2 mm on bottom) with the mucosal surface upward to create a double well culture disk with the small intestinal submucosa acting as the separating membrane. The mucosal surface of the small intestinal submucosa forms the base of the upward facing well while its serosal surface forms the base of the bottom well. The upper well folds 500 ìl of media and the bottom well holds 200 ìl. Following seeding of cells, small intestinal submucosa disks were placed in a 12 well cell culture dish filled with media to allow free contact of the media with both surfaces of the small intestinal submucosa.

Seeding of Urothelial Cells and Smooth Muscle Cells on Small Intestinal Submucosa Disks.

Figure 5:
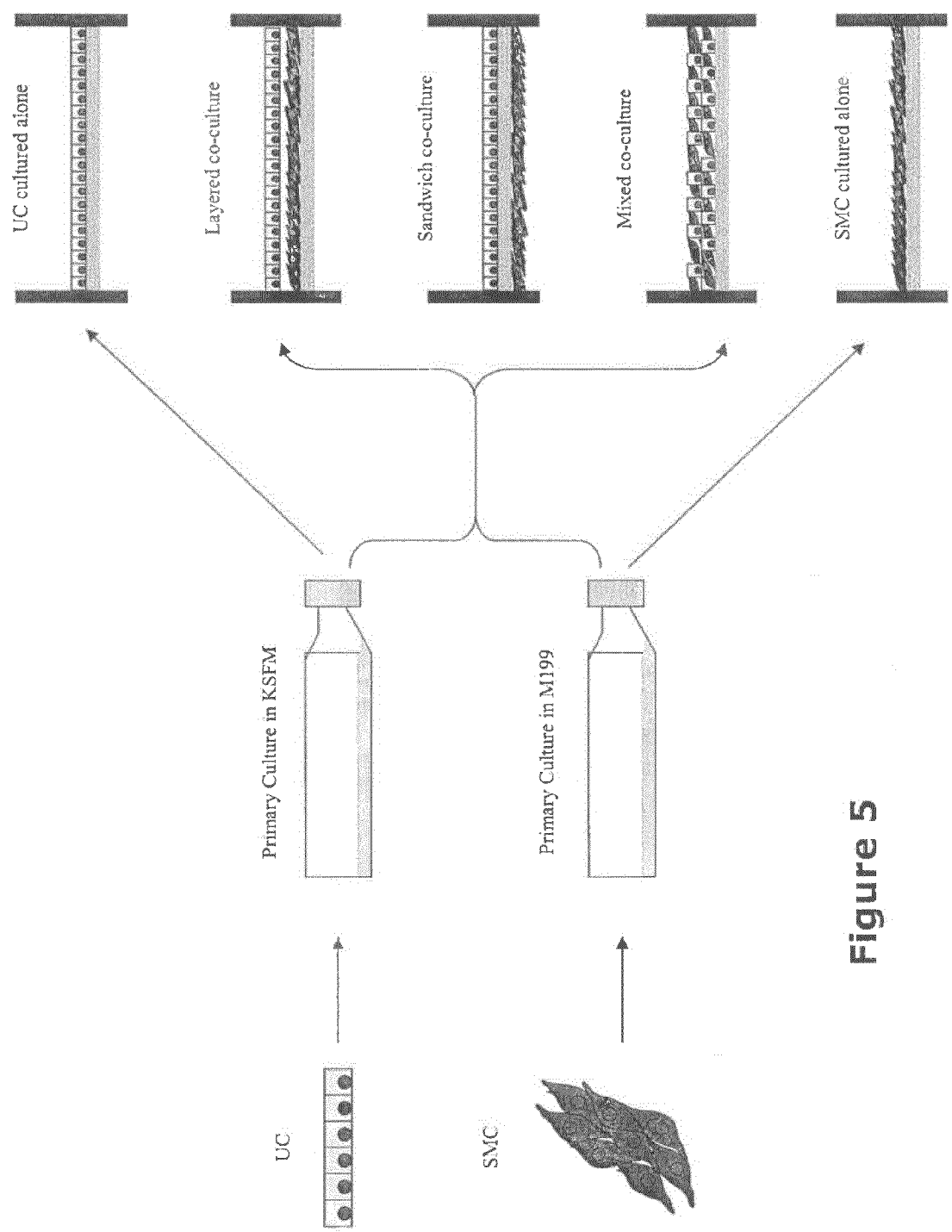
FIG. 5 is a schematic representation of the experimental design for optimizing coculture conditions. Primary cultured bladder urothelial (UC) and smooth muscle cells (SMC) were seeded alone on small intestinal submucosa or in combination with various coculture techniques. KSFM, keratinocyte serum-free media.

A diagram of the experimental design is shown in FIG. 5. Five separate groups were evaluated differing in the method of cell seeding. The first two groups were composed of urothelial cells and smooth muscle cells seeded individually on the mucosal surface of the small intestinal submucosa disks. Cells were seeded at a concentration of $10^5$ cells per cm (Kropp et al., Urology, 52:138 (1998)). To evaluate the effect of different calcium concentrations on the type of growth of urothelial cells on small intestinal submucosa, cells were maintained in keratinocyte serum-free media containing 0.09 mM and 2 mM calcium. The latter is a more physiological level of calcium that had previously been shown to support a more differentiated growth pattern of urothelial cells (Southgate et al., *Lab Invest.* 71:583 (1994)). Smooth muscle cells were maintained in modified M199.

The last three groups were made up of different coculture methods, which included one layered coculture of smooth muscle cells seeded on the mucosal surface of the small intestinal submucosa followed by seeding of urothelial cells on top of the smooth muscle cells one hour later, sandwich coculture of smooth muscle cells seeded on the serosal surface of the small intestinal submucosa disk followed by seeding of the mucosal surface with urothelial cells 24 hours later, and mixed coculture of smooth muscle cells and urothelial cells mixed together and then seeded together on the mucosal surface of the small intestinal submucosa disk. In each coculture group, cells were seeded at a density of $10^5$ cells per cm$^2$ in a medium composed on keratinocyte serum-free media and M199 mixed 1:1. Within each group cells were seeded, incubated and harvested at 3, 7, 14 and 28 days following seeding. For each separate seeding method, 3 separate disks were seeded and harvested at each time point. Once the cells were seeded on the small intestinal submucosa membrane, the medium was changed daily.

Histology and Immunohistochemistry.

At the designated time points small intestinal submucosa disks were harvested and fixed in 10% neutral buffered formalin for 24 hours. To preserve cell integrity and architecture during histological sectioning, the cell-small intestinal submucosa constructs were embedded in 4% agar and then processed for routine histology. Sections were routinely stained with hematoxylin and eosin, and Masson trichrome. To assist in identification of smooth muscle cells and urothelial cells in the coculture groups, immunohistochemical staining was performed with monoclonal antibodies to á-smooth muscle actin (1:1,000) and cytokeratin AE1/AE3 (1:100) which are specific for smooth muscle cells and urothelial cells, respectively. Cells were individually stained with á-smooth muscle actin and double stained with both antibodies using a double stain kit. Variables evaluated at each time point in each group were cell morphology, cell proliferation and layering, cell sorting, presence or absence of pseudostratified urothelium and matrix penetrance of the small intestinal submucosa membrane with smooth muscle cells.

Loading the Tissue Culture Frames with Small Intestinal Submucosa Membrane.

The intact small intestinal submucosa membrane was prepared in a standard method. Briefly, mesenteric tissue was removed from porcine jejunum. The mucosa and lamina propria of the luminal side and the serosa and external muscle layers of the abluminal side were removed mechanically. The resultant submucosa (approx. 0.2 cm thick) was rinsed extensively in water and disinfected with 0.1% peracetic acid solution and 20% ethanol for two hours.

Two types of tissue culture frames were used for preparing small intestinal submucosa membrane as a scaffold: a rabbet-joint frame and a pin frame, as described in detail U.S. Pat. No. 7,122,200, previously incorporated herein by reference. Both of the tissue culture frames described in the '200 patent create a double-chamber with the small intestinal submucosa acting as the separating membrane. The up-well holds approximately 15 ml of media and the bottom-well holds about 20 ml. Both of the tissue culture frames were designed to provide even mechanical strains on the small intestinal submucosa membrane so that the cells are able to attach and grow on the small intestinal submucosa suspended therein.

Growth of BSMC and UC on Small Intestinal Submucosa Membranes.

Dog bladder epithelial and smooth cells were individually seeded onto the tissue culture frames with intact small intestinal submucosa membrane using coculture technique. UC were seeded on SMC layers one hour after SMC were seeded on small intestinal submucosa matrix in the mixture media of KSFM and M199 (KFSM-M199), and the cells were cultured for 14 days.

Small pieces of cell-seeded SIS grafts were cut for histological examination before being implanted back into the host animal.

Animal Operation

Using the canine subtotal cystectomy model, animals underwent urinary bladder augmentations with unseeded SIS grafts, and were directly compared to animals receiving urinary bladder augmentation with seeded SIS grafts. Using methods described in our previous study (Kropp, 1998), cystometrograms (CMG), cystograms, IVU's, and serum chemistries were performed on animals pre-operatively and at 10 weeks post-implantation of the seeded or unseeded SIS to assess upper and lower urinary tract function.

The cell-seeded SIS regenerated bladders were harvested 10 weeks after augmentation and fixed in 10% neutral buffered formalin over 24 hours. The tissue samples were studied with hematoxylin-eosin and immunohistochemical staining.

Results/Discussion

A seeded graft is desired to have proliferating cells that are well attached and growing within the matrix of the biomaterial to prevent slough during the augmentation procedure, as well as to resemble normal bladder tissue. In addition, it has been shown that different biomaterials require different seeding methods for optimization of cell growth and regeneration. To determine the optimal cell seeding density, the optimal amount of time of in vitro culture post-seeding, and the best method of co culture of bladder cells to yield the best biomaterial-cell composite for placement into the host animal, human smooth muscle and urothelial cells were seeded at different densities and with different coculture methods on SIS (FIG. 5), and a number of parameters, such as cell morphology, cell adherence, cell proliferation, the development of a stratified urothelium, and the degree of smooth muscle cell invasion into the membrane, were analyzed.

Primary cultures of human smooth muscle and urothelial cells were established utilizing standard explant techniques as previously described (Cilento et al., *J. Urol.* 152:665 (1994); Baskin et al., *J. Urol.* 149:190 (1993)). Bladder cells were subcultured and expanded as per routine. Smooth muscle and urothelial cells were seeded both individually and together onto intact SIS membranes (100,000-300,000 cells/membrane) and allowed to grow for up to 25 days. Cell growth on intact SIS was compared to growth on conventional plastic. Smooth muscle cells seeded onto intact SIS grew in an organized fashion in three dimensions in multiple cell layers with limited areas of matrix penetration (FIG. 6). Urothelial cells also readily adhered to SIS and grew in multiple layers (FIG. 7).

Figure 8:
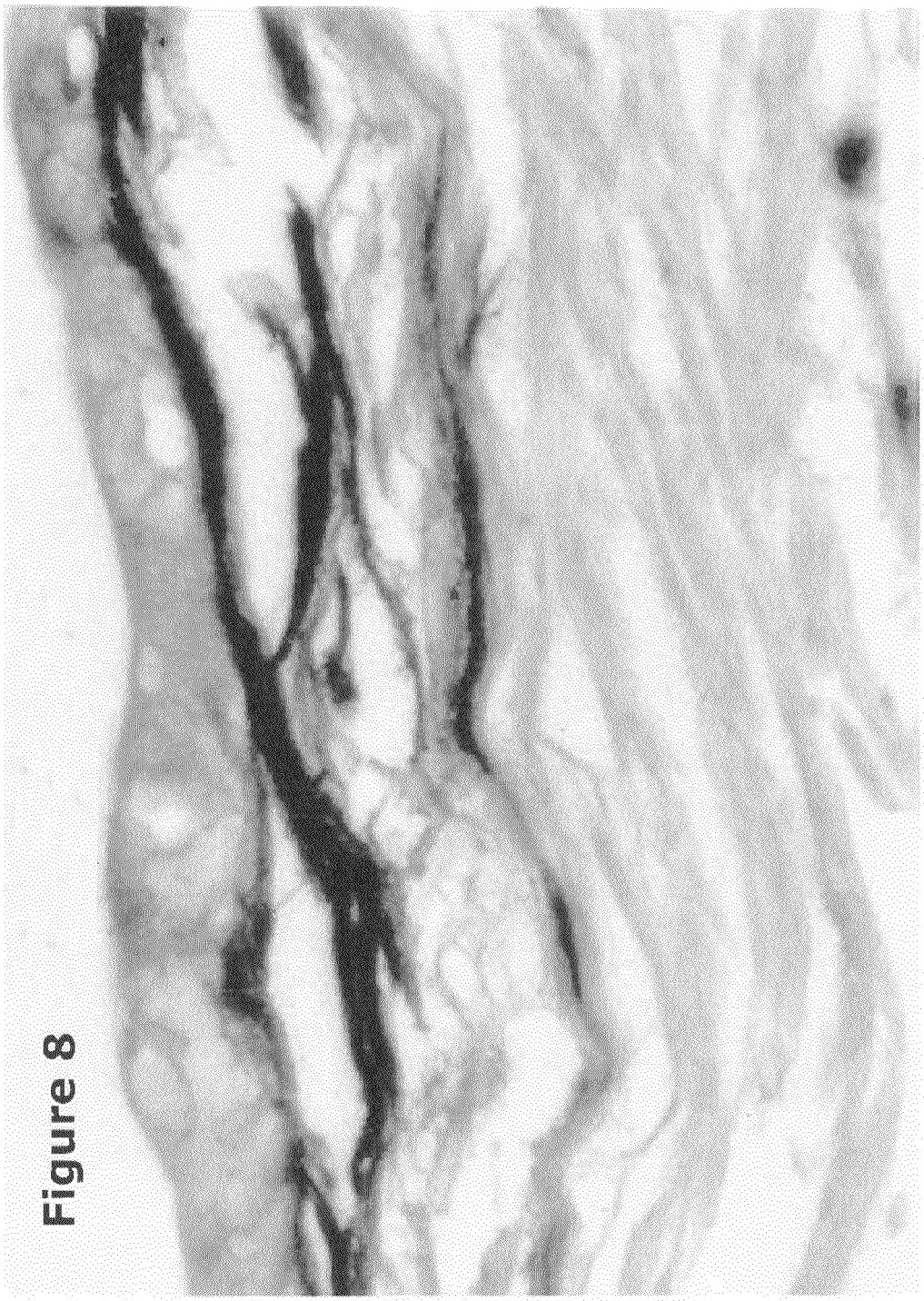
FIG. 8 is photomicrographs illustrating layered coculture. A, at 7 days there is distinct cell sorting confirmed by immunohistochemical analysis and urothelial cells (red staining for cytokeratin AE1/AE3) grow on top of smooth muscle cells (black staining for á-smooth muscle actin), that are beginning to penetrate (arrow) matrix of small intestinal submucosa membrane. Reduced from ×63. B, layered coculture at 28 days reveals further development of pseudostratified layer of urothelial cells growing on top of small intestinal submucosa (open arrow). Smooth muscle cells have now penetrated matrix of small intestinal submucosa and majority of cells are below its surface (solid arrow). Note several areas where smooth muscle cells traverse deep into small intestinal submucosa membrane. This consistent pattern of matrix penetrance of small intestinal submucosa membrane by smooth muscle cells is distinctly different from minimal penetrance seen when smooth muscle cells are grown alone on small intestinal submucosa. Reduced from ×94.
Figure 9:
FIG. 9 is a photomicrograph illustrating sandwich coculture. At 28 days, this method shows similar growth pattern to layered coculture technique except that the urothelial cells and smooth muscle cells are on opposite sides of the small intestinal submucosa membrane. Pseudostratified layer of urothelium is on mucosal surface (open arrow) while multiple layers of smooth muscle cells are on the serosal surface and are penetrating into the matrix of the small intestinal submucosa membrane (solid arrow). Reduced from ×94.
Figure 10A:
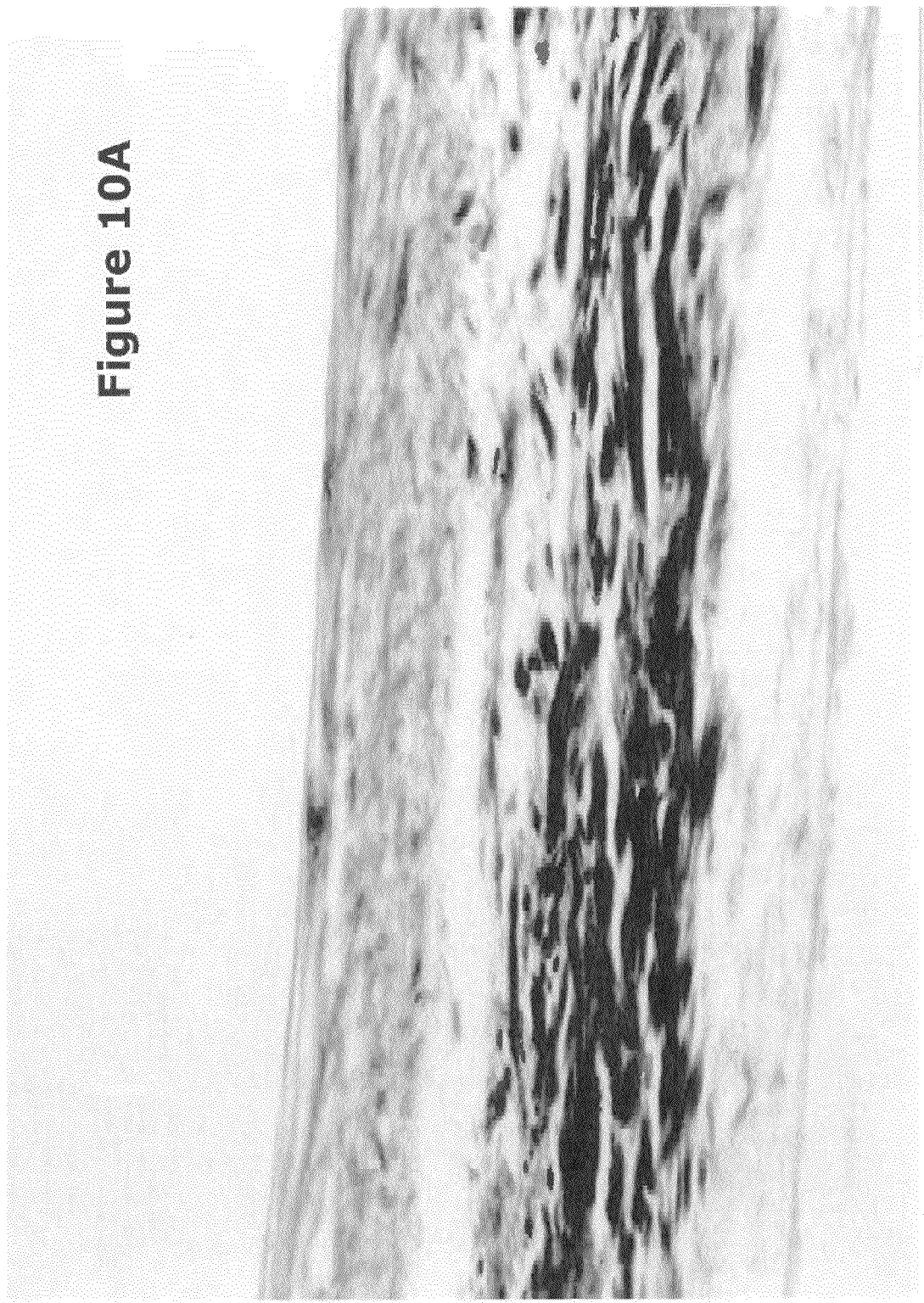
FIG. 10 is photomicrographs illustrating mixed coculture. A, at 28 days there are several layers of cells growing on top of the small intestinal submucosa with active matrix penetration of its membrane. Trichrome, reduced from ×94. B, immunohistochemical analysis (urothelial cells stain red for cytokeratin AE1/AE3 and smooth muscle cells stain black for á-smooth muscle actin) shows lack of cell sorting. Reduced from ×94.
Figure 10B:
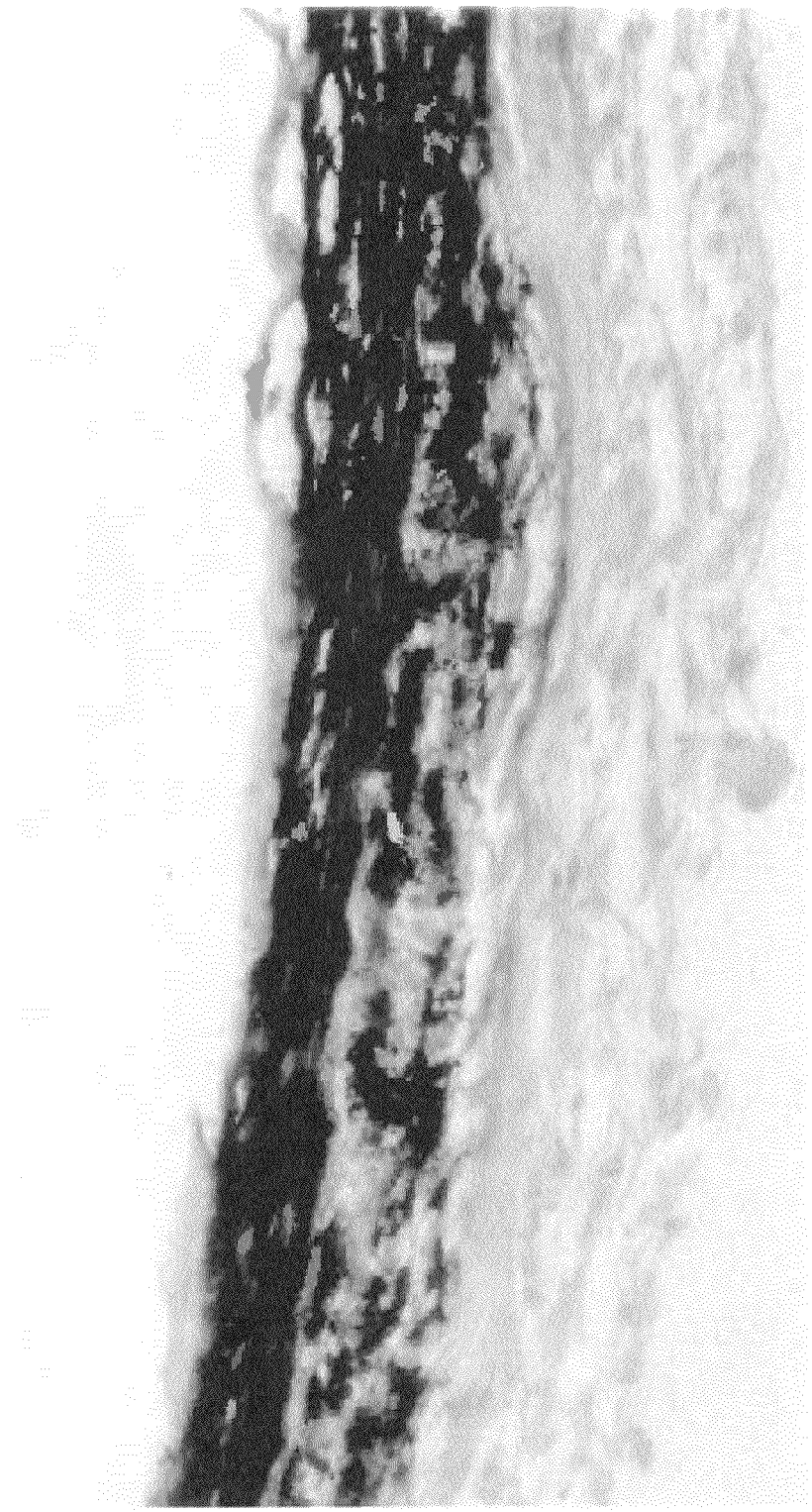

This growth pattern was distinctly different from the two-dimensional monolayer growth pattern that occurs when cells are grown on conventional plastic. When bladder smooth muscle and urothelial cells were plated together, there was a synergistic effect with regard to enhanced growth and penetration of the SIS membrane (FIGS. 8 and 9). Immunohistochemical staining patterns of smooth muscle cells (á smooth muscle actin and smooth muscle myosin) and epithelial cells (cytokeratin 8.12/8.13) were preserved when grown on intact SIS.

As there was no standardized method in the literature and emboldened by the success of experiments which demonstrated that it is possible to grow bladder cells on SIS in long-term tissue culture, a more thorough characterization of the culture conditions which yielded the best seeded graft on the basis of histological and immunohistochemical analysis were undertaken. Five different methods of seeding and culture were assessed at time points of 3, 7, 14 and 28 days to establish which method was most effective at developing a usable graft in the shortest period of time. It was found that grafts made by sequential seeding coculture of SMC and UC (with SMC seeded on the membrane one hour prior to over-seeding UC on the same surface of the membrane) for 14 days resulted in the most differentiated graft (FIG. 8). In addition, the sandwich coculture technique (FIG. 9) also resulted in organized cell sorting, formation of a well-defined pseudostratified urothelium and multilayered smooth muscle cells with enhanced matrix penetration. With the mixed coculture technique (FIG. 10), there was no evidence of cell sorting, although matrix penetrance by the smooth muscle cells was evident.

It was also established that there are SMC/UC interactions that are involved in the determination of the type of growth seen on the membrane (proliferative vs. differentiative, invasive vs. surface limited), and that it is necessary for the cells to be in physical contact with each other to achieve the most "tissue-like" appearance in culture. The presence of urothelial cells significantly impacts the pattern of smooth muscle cell growth on small intestinal submucosa since active penetrance of the membrane only occurs when urothelial cells are grown in conjunction with smooth muscle cells.

To assess the effect of cell density on graft development, the seeding density of the SMC and UC on the SIS membrane was varied and cultured for the period previously shown to yield optimum histological organization. After 14 days of culture, the grafts were harvested for comparative histology. It was determined that while the higher seeding density yielded a thicker layer of cells on the surface of the membrane (1-2 layers more cells), that invasion into the interstices of the membrane by SMCs was significantly enhanced in the $10^5$ cells/cm$^2$ cultures. The lowest seeding density had a paucity of cells which were limited to the surface of the membrane with no evidence of invasion. We feel that a compelling case can be made for using the culture parameters outlined to create our material for re-implantation into the animal. First, using a medium density seeding allows us to generate enough cells to do the procedure in a shorter period of time. Second, the medium density cultures have a more tenacious hold on the membrane and are less likely to be abraided from the graft due to manipulation during the re-implantation process, thereby leaving more cells to participate in the regenerative process. Finally, with the medium density cell inoculum, the process of tissue reorganization has already begun to occur in culture. Thus, the graft is further along in the regenerative process and this should lead to a faster regeneration of functional bladder tissue in the host animal.

In summary, the best method of seeding was achieved by first seeding the mucosal surface of the graft with smooth muscle cells followed by urothelial cells one hour later. The optimal seeding density was 100,000 cells/cm$^2$. This seeding method yielded a seeded graft that had the best histologic characteristics relative to normal bladder. There was a well developed pseudostratified urothelium with multiple layers of smooth muscle cells proliferating within the matrix of the SIS membrane. Additionally, it was determined that after 14 days in culture the seeded graft does not further mature and differentiate when carried out to 28 days.

Once the coculture conditions were optimized using the small intestinal submucosa disks, such coculture conditions were applied to a large-scale study in which 7×10 cm segments of small intestinal submucosa were suspended in the two tissue culture frames described herein above, and dog bladder smooth muscle and urothelial cells were seeded thereon by the layered coculture method described above. Both of the tissue culture frames are user-friendly and easy to clean, sterilize, and store and do not affect cell growth or differentiation.

Figure 11:
FIG. 11 is a photomicrograph illustrating layered coculture of dog bladder epithelial and smooth muscle cells on small intestinal submucosa membrane before implanting of graft. At 14 days there are several areas where smooth muscle cells traverse deep into small intestinal submucosa membrane and epithelial cells grow on the top of smooth muscle cells (Masson Trichrome staining ×20).

On day 14, the urothelial cells were flattened in shape and grew on top of the smooth muscle cells, which were spindle shaped. Distinct cell sorting was noted in which the smooth muscle cells grew on top of the SIS with early matrix penetrance, while the urothelial cells grew on top of the smooth muscle cells as a separate population of cells. The SMC layer was up to 5-7 layers thick. The vast majority of SMC were no longer on the surface of the SIS. Rather, they had penetrated the matrix of the SIS membrane and were now proliferating under the surface of the SIS within the membrane. In several areas, SMC could be seen traversing into the deep portions of the SIS membrane (FIG. 11).

Figure 12:
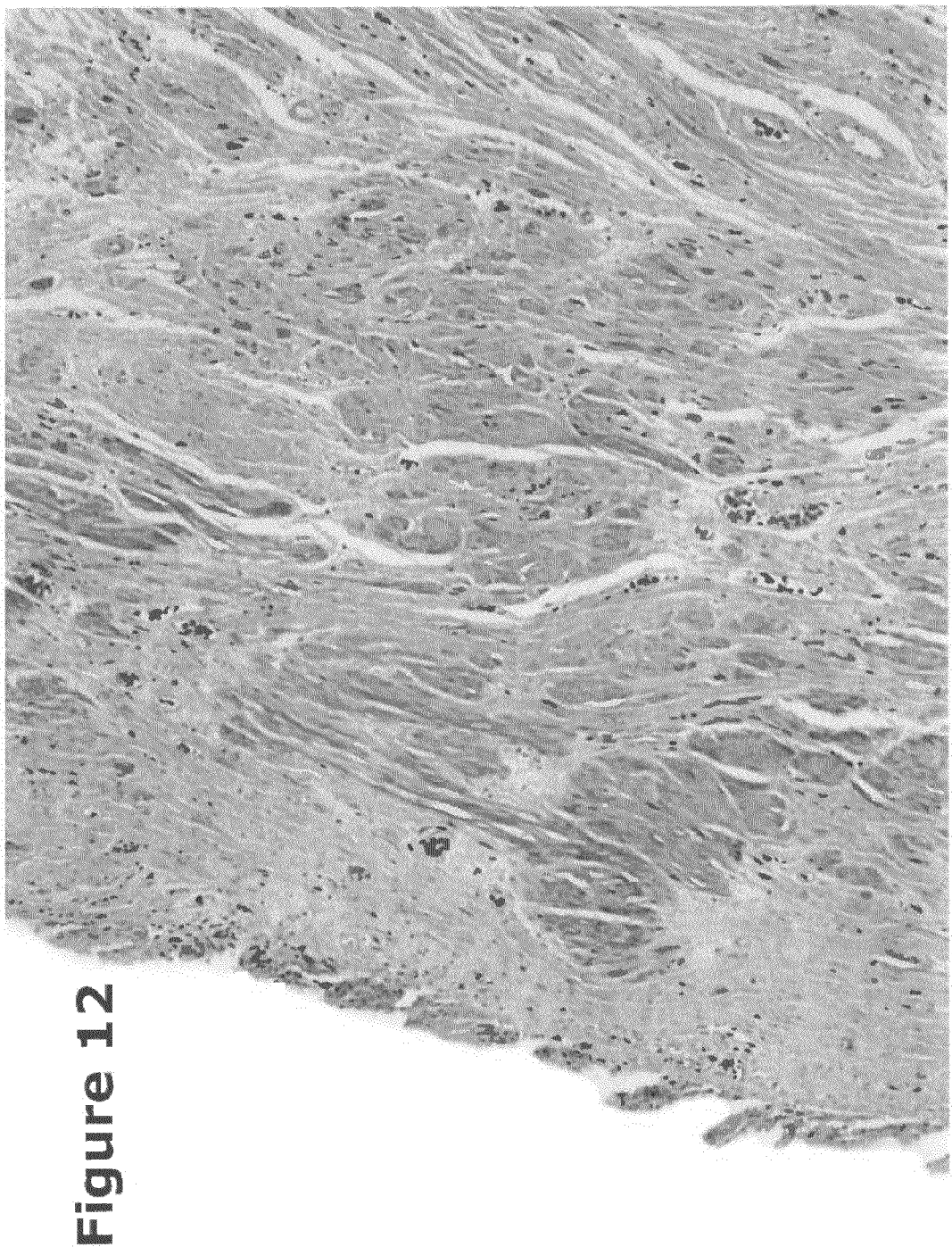
FIG. 12 is a photomicrograph of Masson trichrome stained cell-seeded small intestinal submucosa regenerated dog bladder at 10 weeks postaugmentation. All layers of bladder are present. Abundant smooth muscle bundle formations (red) are surrounded by collagenous matrix (blue). ×20.

Ten weeks after augmentation, the cell-seeded grafts had grossly minimal adhesions to the surrounding perivesical fat or other intra-abdominal structures. Histologically, the SIS grafts were completely covered by urothelial cells. Grafts showed a prominent neovascularization at their edges and infiltration of their entire surface by the new capillaries. Regenerated smooth muscle bundle formation was present and indistinguishable from the normal native bladder (FIG. 12).

Example 3

Materials and Methods

The SIS was obtained in a dry form as 10 cm×7 cm rectangles from Cook® Biotech Inc. (W. Lafayette, Ind.). Poly (lactic-co-glycolic) acid (PLGA) was purchased from Absorbable Polymers International (Pelham, Ala.) as a 50:50 monomer ratio with molecular weight of 106 kD and viscosity of 1.05 dL/g. Latex spheres and urea were obtained from Sigma-Aldrich (St. Louis, Mo.). The urea assay kit (catalogue #275-13) was purchased from Diagnostics Chemicals Limited, Oxford, Conn. All chemical reagents used were purchased from Fisher Scientific (Pittsburgh, Pa.).

Synthesis of Nanoparticles

PLGA nanoparticles (NPs) were synthesized using a double emulsion solvent evaporation technique. Briefly, 30-40 mg of PLGA was dissolved in 1 mL chloroform. 200 µL of double distilled water (DD H$_2$O) was added to the PLGA and sonicated with a probe sonicator model VC60 (Sonics & Materials, Danbury, Conn.) for 30 seconds at 100% of amplitude on a continuous mode. This primary emulsion was then dropped in 10 mL of 1% polyvinyl alcohol (PVA) and sonicated with the same probe sonicator for 1 min at 100%. The final solution was stirred on a magnetic plate overnight to allow for the complete evaporation of the organic solvent. The PLGA NPs were then spun down at 11,000 rpm at 4 C for 20 min using centrifuge model RC5C+ (Sorvall, Asheville, N.C.). The pellet was weighed and washed 3 times with DD H$_2$O to wash away any remaining PVA. PLGA NPs were then resuspended in DD H$_2$O, volume depending on the concentration desired. The NPs were used on the same day.

Nanoparticle Characterization

Diffraction light scattering was used to determine the size, polydispersity index, and zeta potential measurement (Zeta-PALS, Brookhaven Instruments, Holtsville, N.Y.). Measurements were performed at 25 C. The viscosity and refraction index were set equal to those specific for water. Measurements were made in disposable cuvettes with a volume of 4 mL.

Permeability Studies

To evaluate the permeability of the SIS membranes, a custom-made chamber with a diameter of 2 cm was used. The chambers on either side of the membrane can hold a maximum volume of 4 mL each. The first chamber refers to the chamber facing the mucosal side of the SIS, and the second chamber refers to the chamber facing the serosal side. Latex spheres in PBS were placed in the first chamber, and PBS was placed in the second chamber. The permeability chambers were incubated overnight at 37 C in an orbital shaker at 125 rpm in a position where the first chamber is on top of the second chamber. The chambers were then washed once with PBS to avoid the interference of the particles with the permeability studies. In the first chamber, 550 mM urea in PBS was added (based on the average physiological concentration in urine). PBS was added to the second chamber. The chambers were incubated at 37 C in a standing position. At different time points, small samples (20-50 µL) were collected from the second chamber up to 2 hours. Samples collected immediately after the assembly of the unit were used as time-zero values (i.e. $C_2$ at t=0). The concentration of urea was determined using a commercially available kit following the vendor's protocol. Briefly, 20-30 µL of sample (with or without dilution) was added to 2 mL of urease solution, and the rate of change in absorption at 340 nm was measured for 90 seconds. Standards with concentrations between 0 and 275 mM were used to construct the calibration curve. The concentration of urea in the samples was determined by comparing to the calibration curve. To determine the permeability of the membrane to urea, a quasi steady-state was assumed where the following equation was used:

$$\ln = \left[\frac{C_1 - 2C_2}{C_1}\right] \equiv -\left[\frac{A_m}{V}\frac{D_m\varphi}{L}\right]t = -\left[\frac{A_m}{V}P\right]t$$

where $C_1$ is the initial concentration of urea which is 550 mM and $C_2$ is the concentration of urea at time t. $A_m$ is the membrane area=$\pi$cm$^2$, V is the volume of the chamber=4 mL, $D_m$ is the diffusion coefficient, $\phi$ is the partition coefficient, L is the thickness of the membrane, and P is the permeability.

$$P = \frac{D_m\phi}{L}$$

Then ln $$\ln\left[\frac{C_1 - 2C_2}{C_1}\right]$$

was plotted as a function of time t from which the $$\text{slope} = \frac{A_m}{V}P$$

was determined using a linear fit. The permeability was determined from the slope values.

Results/Discussion

Figure 13:
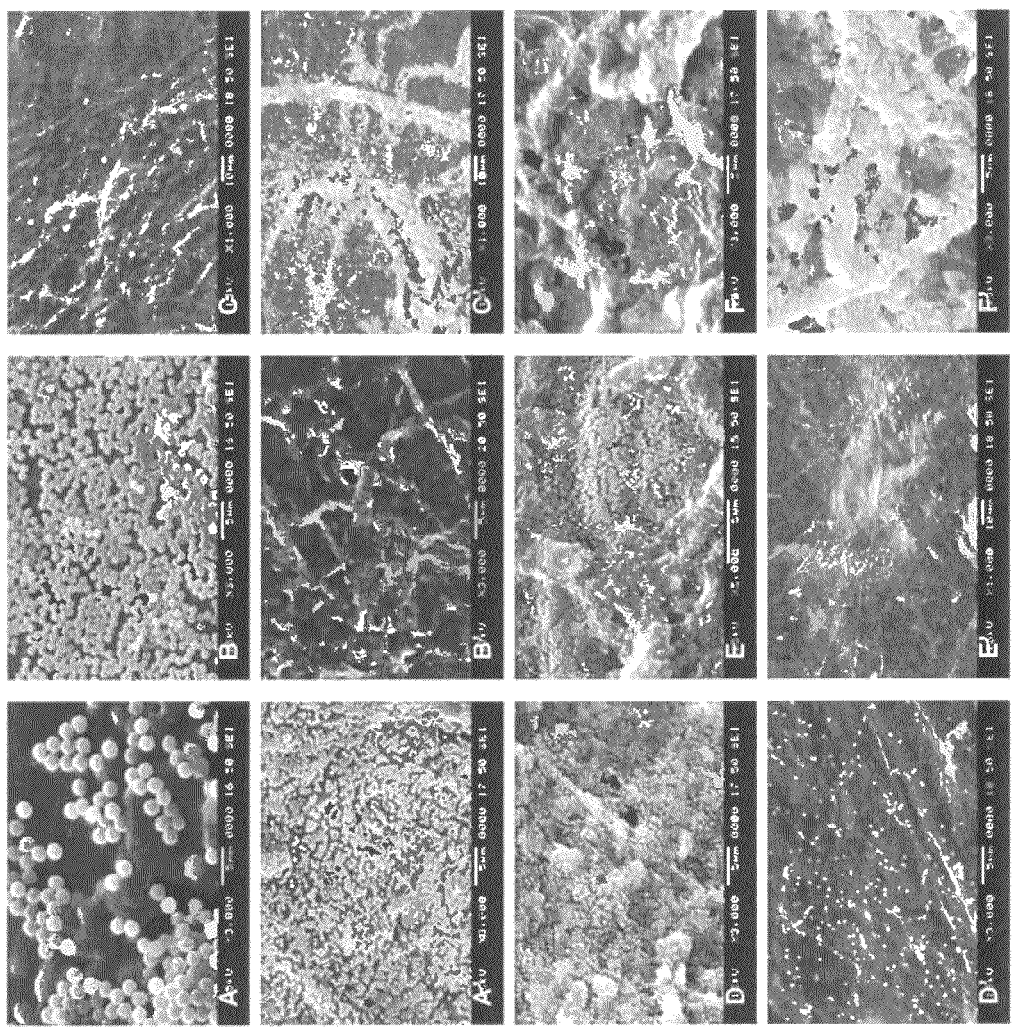
FIG. 13 contains scanning electron micrographs (SEMs) of SIS after overnight incubation with latex spheres. Panels A and A' illustrate the mucosal and serosal sides of SIS, respectively, after incubation with 2 µm latex particles. Similarly, the remaining panels illustrate the mucosal and serosal sides of SIS after incubation with other sizes of latex particles: Panels B and B' are with 1 µm latex particles; Panels C and C' are with 500 nm latex particles; Panels D and D' are with 300 nm latex particles; Panels E and E' are with 200 nm latex particles; and Panels F and F' are with 50 nm latex particles.

Because of the limitations with making PLGA nanoparticles using the double emulsion method, latex spheres were first used to determine the size range that will go through the SIS. These latex spheres were 2 im, 1 im, 500 nm, 300 nm, 200 nm and 50 nm. These latex spheres are commercially available and exhibit a low polydispersity index. Scanning electron microscopy (SEM) images were taken for both sides of the SIS after being rinsed with DD H$_2$O, as shown in FIG. 13. It can be seen that the latex spheres with diameters ranging from 200 to 500 nm went all the way through the SIS, thus suggesting that some were trapped within the SIS. The 50 nm latex spheres must have also gone through the entire SIS. The reason that no latex particles are seen on the other side is most likely because they were too small to be trapped anywhere in the SIS.

Figure 14:
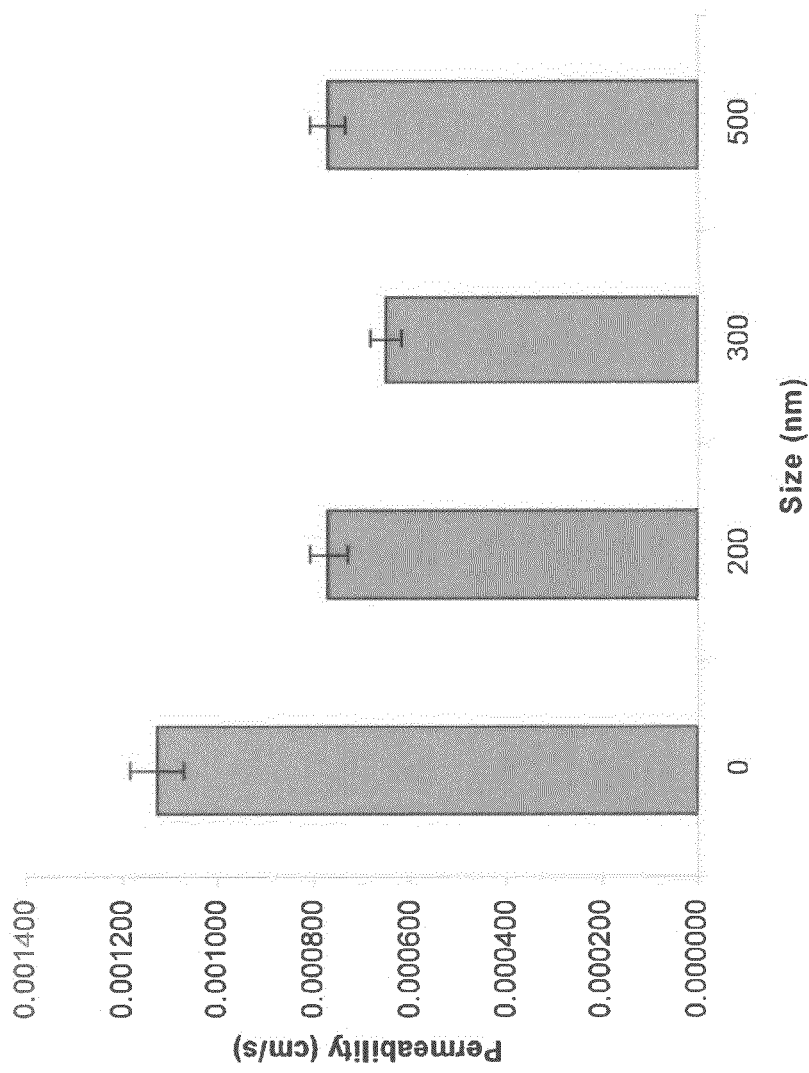
FIG. 14 graphically illustrates the permeability of treated SIS to urea, wherein the SIS was treated by incubation with latex spheres. Zero on the size axis denotes the control where the permeability of SIS to urea was measured without incubation of the SIS with latex particles.

The permeability of the modified SIS to urea was then measured to see if the latex particles had any effect. FIG. 14 demonstrates how the permeability changed as compared to the control (with no latex spheres). It can be seen that the permeability dropped for the 200 nm latex spheres but increased for the 500 nm latex spheres. This confirms the results seen in the SEM images, namely, that the desired size range for the latex spheres is 200-500 nm.

Figure 15:
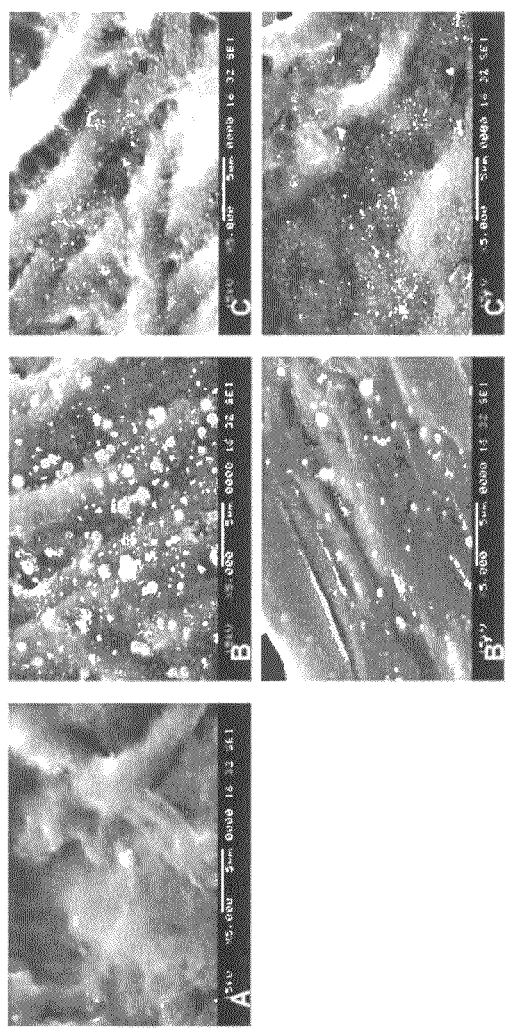
FIG. 15 contains SEMs of SIS after overnight incubation with poly(lactic-co-glycolic) acid (PLGA) nanoparticles (NPs). Panels B and B' show the mucosal and serosal sides of the SIS, respectively, after incubation with 306 nm PLGA NPs. Similarly, Panels C and C' are the mucosal and serosal sides of the SIS, respectively, after incubation with 163 nm PLGA NPs. Panel A is the control.

Next, similar experiments were performed using PLGA NPs. FIG. 15 illustrates SEM images of both the mucosal and serosal sides of the SIS that were incubated with 306 nm and 162 nm PLGA NPs, as well as SEM images of the control (without PLGA NPs). These SEM images verify that PLGA NPs went all the way through the SIS, causing some to be entrapped within the SIS.

The permeability of the SIS to urea was then measured after introducing the PLGA NPs. For these experiments, one size of PLGA NPs was used at different concentrations. Even though the degradation products of the PLGA NPs—lactic acid and glycolic acid—are normal byproducts of metabolic pathways in the body, they are still acidic. Thus, some concerns have been raised that too much PLGA NPs might harm the cells. FIG. 16 shows the results from 2 sets of experiments.

Thus it should be apparent that there has been provided in accordance with the present invention a tissue graft composition, a method of providing a tissue graft composition, and a method for repairing a damaged tissue of a subject, that fully satisfies the objectives and advantages set forth above. Although the invention has been described in conjunction with specific embodiments thereof, it is evident that many alternatives, modifications, and variations will be apparent to those skilled in the art. Accordingly, it is intended to embrace all such alternatives, modifications, and variations that fall within the spirit and broad scope of the description and claims.

What is claimed is:

1. A biodegradable tissue graft composition, comprising:
   a segment of small intestinal submucosa;
   at least one biodegradable nanoparticle incorporated into the segment of small intestinal submucosa, the biodegradable nanoparticle having a size of from about 200 nm to about 500 nm, wherein the biodegradable nanoparticle has at least one macromolecule incorporated therein, and wherein the biodegradable nanoparticle exhibits controlled release of the at least one macromolecule incorporated therein; and
   wherein the tissue graft composition has decreased permeability when compared to the segment of small intestinal submucosa alone.

2. The biodegradable tissue graft composition of claim 1, wherein the segment of small intestinal submucosa consists essentially of a distal ileal segment of small intestinal submucosa isolated from a mature adult pig.

3. The biodegradable tissue graft composition of claim 1, wherein the at least one macromolecule is selected from the group consisting of growth factors, hormones, nucleic acids, polysaccharides, drugs, and combinations thereof.

4. The biodegradable tissue graft composition of claim 1, wherein the at least one nanoparticle is selected from the group consisting of poly(lactic-co-glycolic) acid (PLGA) nanoparticles, poly lactic acid (PLA) nanoparticles, chitosen nanoparticles, liposomes, and combinations thereof.

5. The biodegradable tissue graft composition of claim 1, further defined as a biodegradable urinary tract tissue graft composition.

6. The biodegradable tissue graft composition of claim 5, further comprising at least one cell type seeded on a surface of the segment of small intestinal submucosa, wherein the at least one cell type is selected from the group consisting of smooth muscle cells, urothelial cells and stem cells.

7. The biodegradable tissue graft composition of claim 6, wherein smooth muscle cells are seeded on a mucosal surface of the segment of small intestinal submucosa, and urothelial cells are seeded on a serosal surface of the segment of small intestinal submucosa.

8. The biodegradable tissue graft composition of claim 6, wherein smooth muscle cells are seeded on a mucosal surface of the segment of small intestinal submucosa, and wherein urothelial cells are seeded upon the smooth muscle cells on the mucosal surface of the segment of small intestinal submucosa.

9. A kit, comprising:
the biodegradable tissue graft composition of claim 1; and
means for suspending the biodegradable tissue graft composition and holding the biodegradable tissue graft composition in a taut position such that cells may be seeded thereon.

10. The kit of claim 9, wherein the means is a tissue culture frame.

11. The kit of claim 9, wherein the segment of small intestinal submucosa consists essentially of a distal ileal segment of small intestinal submucosa isolated from a mature adult pig.

12. The kit of claim 9, wherein the at least one macromolecule is selected from the group consisting of growth factors, hormones, nucleic acids, polysaccharides, drugs, and combinations thereof.

13. The kit of claim 9, wherein the at least one nanoparticle is selected from the group consisting of poly(lactic-co-glycolic) acid (PLGA) nanoparticles, poly lactic acid (PLA) nanoparticles, chitosen nanoparticles, liposomes, and combinations thereof.

14. A method for repairing a damaged tissue of a subject, comprising the steps of:
providing the biodegradable tissue graft composition of claim 1; and
contacting the damaged tissue with the biodegradable tissue graft composition under conditions such that growth of the tissue occurs and the damaged tissue is repaired, thereby restoring function to the tissue.

15. The method of claim 14 wherein, in the step of providing the biodegradable tissue graft composition, the segment of small intestinal submucosa consists essentially of a distal ileal segment of small intestinal submucosa isolated from a mature adult pig.

16. The method of claim 14 wherein, in the step of providing the biodegradable tissue graft composition, the at least one macromolecule is selected from the group consisting of growth factors, hormones, nucleic acids, polysaccharides, drugs, and combinations thereof.

17. The method of claim 14 wherein, in the step of providing the biodegradable tissue graft composition, the at least one nanoparticle is selected from the group consisting of poly(lactic-co-glycolic) acid (PLGA) nanoparticles, poly lactic acid (PLA) nanoparticles, chitosen nanoparticles, liposomes, and combinations thereof.

18. The method of claim 14 further comprising the steps of:
isolating and culturing at least one cell type from a tissue specimen of a subject;
seeding the at least one cell type on the biodegradable tissue graft composition; and
allowing the biodegradable tissue graft composition having the at least one cell type seeded thereon to mature in culture such that the at least one cell type exhibits three dimensional growth and matrix penetrance, prior to contacting the damaged tissue with the biodegradable tissue graft composition.

19. The method of claim 18, wherein the at least one cell type is selected from the group consisting of smooth muscle cells and urothelial cells.

20. The method of claim 18, wherein the damaged tissue is a damaged urinary tract tissue.

* * * * *

UNITED STATES PATENT AND TRADEMARK OFFICE
CERTIFICATE OF CORRECTION

PATENT NO. : 8,974,810 B2  Page 1 of 2
APPLICATION NO. : 13/195400
DATED : March 10, 2015
INVENTOR(S) : Bradley P. Kropp et al.

Figure 8A:
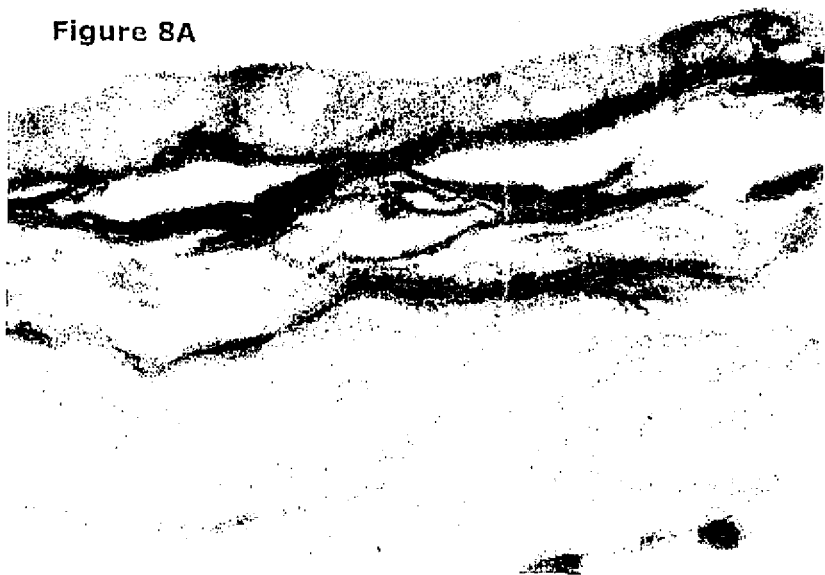

It is certified that error appears in the above-identified patent and that said Letters Patent is hereby corrected as shown below:

In the Drawings: Replace sheet 9 of 19; Replace FIG. 8 with FIG. 8A

Signed and Sealed this
Fourteenth Day of July, 2015

Michelle K. Lee
*Director of the United States Patent and Trademark Office*